(12) United States Patent
Voisard et al.

(10) Patent No.: US 9,603,646 B2
(45) Date of Patent: Mar. 28, 2017

(54) BONE FIXATION ASSEMBLY

(71) Applicant: DePuy Synthes Products, Inc., Raynham, MA (US)

(72) Inventors: Cyril Voisard, Niederbipp (CH); Azagen Mootien, Rantzwiller (FR); Etienne Crozier, La Neuveville (CH); Jean-Luc Thuliez, Le Landeron (CH); Nicolas Obliger, Pin (FR)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/704,658

(22) Filed: May 5, 2015

(65) Prior Publication Data

US 2015/0342657 A1    Dec. 3, 2015

Related U.S. Application Data

(60) Provisional application No. 62/005,552, filed on May 30, 2014.

(51) Int. Cl.
*A61B 17/58* (2006.01)
*A61B 17/60* (2006.01)
(Continued)

(52) U.S. Cl.
CPC ........ *A61B 17/8861* (2013.01); *A61B 17/823* (2013.01); *A61B 17/842* (2013.01);
(Continued)

(58) Field of Classification Search
CPC . A61B 17/8869; A61B 17/8861; A61B 17/82; A61B 17/842
(Continued)

(56) References Cited

U.S. PATENT DOCUMENTS 1,641,077 A * 8/1927 Fouquet .................. B21F 15/00
                                                            140/121
3,111,945 A * 11/1963 Von Solbrig ........... A61B 17/82
                                                            606/103
(Continued)

FOREIGN PATENT DOCUMENTS

DE      3244680      6/1984
DE      3538645      5/1987
(Continued)

*Primary Examiner* — Eduardo C Robert
*Assistant Examiner* — Michelle C Eckman
(74) *Attorney, Agent, or Firm* — Baker & Hostetler LLP

(57) ABSTRACT

A bone fixation system includes at least one bone fixation member and a bone fixation instrument. The bone fixation member includes a strap and a locking mechanism. The strap can be pulled through the locking mechanism so as to form a loop about a target bone so as to secure first and second bone segments in an approximated, compressed configuration. The bone fixation instrument is configured to apply tension to the loop about the target bone. The fixation instrument includes a tension assembly that is configured to secure a free end of the bone fixation member to the fixation instrument. The tension assembly is further configured to pull the free end so as to increase tension in the loop while the tension in the loop is less than a select tension. The tension assembly is unable to further increase tension in the bone fixation member once the tension in the bone fixation member has reached the select tension. The fixation instrument further includes a cutter assembly that is configured to cut the free end of the bone fixation member so as to separate the free end from the loop.

19 Claims, 21 Drawing Sheets

(51) Int. Cl.
  *A61F 2/00* (2006.01)
  *A61B 17/88* (2006.01)
  *A61B 17/82* (2006.01)
  *A61B 17/84* (2006.01)
(52) U.S. Cl.
  CPC ...... *A61B 17/8863* (2013.01); *A61B 17/8869* (2013.01); *A61B 17/8872* (2013.01)
(58) Field of Classification Search
  USPC .................. 606/74, 103, 86 R, 139–141
  See application file for complete search history.

(56) References Cited

U.S. PATENT DOCUMENTS

| | | | |
|---|---|---|---|
| 3,169,560 A | 2/1965 | Caveney et al. | |
| 3,570,497 A | 3/1971 | Lemole | |
| 3,577,601 A | 5/1971 | Mariani et al. | |
| 3,645,302 A * | 2/1972 | Caveney ............... | B65B 13/027 140/123.6 |
| 3,661,187 A * | 5/1972 | Caveney ............... | B65B 13/027 140/123.6 |
| 3,830,263 A * | 8/1974 | Benfer .................. | B21F 9/02 140/123.6 |
| 4,093,005 A * | 6/1978 | Eberhardt ............. | B65B 13/027 140/123.6 |
| 4,535,764 A | 8/1985 | Ebert | |
| 4,730,615 A | 3/1988 | Sutherland et al. | |
| 4,813,416 A * | 3/1989 | Pollak .................. | A61B 17/04 24/16 PB |
| 4,955,913 A | 9/1990 | Robinson | |
| 4,966,600 A * | 10/1990 | Songer ................. | A61B 17/8869 606/103 |
| 5,146,645 A | 9/1992 | Dirksing | |
| 5,146,654 A | 9/1992 | Caveney et al. | |
| 5,193,250 A | 3/1993 | Caveney | |
| 5,355,913 A * | 10/1994 | Green .................. | B65B 13/027 140/123.6 |
| 5,356,417 A | 10/1994 | Golds | |
| 5,361,475 A | 11/1994 | Scruggs | |
| 5,366,461 A | 11/1994 | Blasnik | |
| 5,383,882 A | 1/1995 | Buess et al. | |
| 5,392,822 A * | 2/1995 | Kraus ................... | B65B 13/027 140/123.6 |
| 5,403,346 A | 4/1995 | Loeser | |
| 5,437,685 A | 8/1995 | Blasnik | |
| 5,462,542 A | 10/1995 | Alesi, Jr. | |
| 5,496,318 A | 3/1996 | Howland et al. | |
| 5,540,698 A * | 7/1996 | Preissman ............ | A61B 17/82 606/103 |
| 5,549,619 A | 8/1996 | Peters et al. | |
| 5,571,105 A | 11/1996 | Gundolf | |
| 5,607,430 A | 3/1997 | Bailey | |
| 5,636,412 A | 6/1997 | Lodi et al. | |
| 5,665,088 A | 9/1997 | Gill et al. | |
| 5,665,089 A | 9/1997 | Dall et al. | |
| 5,683,404 A | 11/1997 | Johnson | |
| 5,741,259 A | 4/1998 | Chan | |
| 5,772,663 A | 6/1998 | Whiteside et al. | |
| 5,810,824 A | 9/1998 | Chan | |
| 5,915,425 A * | 6/1999 | Nilsson ................ | B65B 13/027 140/123.6 |
| 5,972,006 A | 10/1999 | Sciaino, Jr. | |
| 6,049,949 A | 4/2000 | Guthke | |
| 6,050,998 A | 4/2000 | Fletcher | |
| 6,099,527 A | 8/2000 | Hochschuler et al. | |
| 6,302,889 B1 | 10/2001 | Keller | |
| 6,443,955 B1 * | 9/2002 | Ahrend ................ | A61B 17/8866 606/103 |
| 6,489,246 B1 | 12/2002 | Summa et al. | |
| 6,514,255 B1 | 2/2003 | Ferree | |
| 6,520,965 B2 | 2/2003 | Chervitz et al. | |
| 6,589,246 B1 | 7/2003 | Hack et al. | |
| 6,752,810 B1 * | 6/2004 | Gao ..................... | A61B 17/8861 606/103 |
| 7,008,429 B2 | 3/2006 | Golobek | |
| 7,112,221 B2 | 9/2006 | Harris | |
| 7,164,360 B2 | 1/2007 | Schiebler | |
| 7,229,444 B2 | 6/2007 | Boyd | |
| 7,481,828 B2 | 1/2009 | Mazda et al. | |
| 7,582,089 B2 | 9/2009 | Schiebler | |
| 7,648,504 B2 | 1/2010 | Heino et al. | |
| 8,992,543 B2 * | 3/2015 | Yamaguchi ......... | A61B 17/8869 606/103 |
| 2003/0236538 A1 | 12/2003 | Aikens | |
| 2004/0059357 A1 | 3/2004 | Koseki | |
| 2004/0068292 A1 | 4/2004 | Koseki | |
| 2005/0137608 A1 * | 6/2005 | Hearn .................. | A61B 17/688 606/103 |
| 2005/0178461 A1 * | 8/2005 | Magno ................. | B65B 13/027 140/123.6 |
| 2006/0135958 A1 * | 6/2006 | Marissen ............. | A61B 17/823 606/74 |
| 2006/0142772 A1 | 6/2006 | Ralph et al. | |
| 2006/0271060 A1 * | 11/2006 | Gordon ............... | A61B 17/0401 606/103 |
| 2007/0055258 A1 | 3/2007 | Hansen | |
| 2007/0093825 A1 | 4/2007 | Ferree | |
| 2007/0260251 A1 * | 11/2007 | Weier .................. | A61B 17/823 606/74 |
| 2008/0027440 A1 * | 1/2008 | Marissen ............. | A61B 17/823 606/74 |
| 2008/0300599 A1 | 12/2008 | Anapliotis et al. | |
| 2009/0012569 A1 | 1/2009 | Dall et al. | |
| 2009/0082776 A1 * | 3/2009 | Cresina ............... | A61B 17/8869 606/103 |
| 2009/0138048 A1 * | 5/2009 | Baccelli .............. | A61B 17/8869 606/263 |
| 2009/0270923 A1 | 10/2009 | Tormala et al. | |
| 2009/0326585 A1 | 12/2009 | Baccelli et al. | |
| 2010/0057091 A1 * | 3/2010 | Oosterom ........... | A61B 17/8861 606/103 |
| 2010/0087836 A1 * | 4/2010 | Jaramillo ............ | A61B 17/04 606/144 |
| 2010/0087837 A1 * | 4/2010 | Jaramillo ............ | A61B 17/04 606/144 |
| 2011/0112537 A1 * | 5/2011 | Bernstein ........... | A61B 17/8869 606/74 |
| 2012/0197256 A1 * | 8/2012 | Knueppel ........... | A61B 17/823 606/74 |
| 2012/0197257 A1 * | 8/2012 | Knueppel ........... | A61B 17/823 606/74 |
| 2013/0116736 A1 * | 5/2013 | De Oliveira ........ | A61B 17/0467 606/86 R |
| 2013/0167334 A1 * | 7/2013 | Gephart .............. | A61B 17/8861 24/69 R |
| 2013/0261625 A1 * | 10/2013 | Koch .................. | A61B 17/1604 606/74 |
| 2014/0142638 A1 * | 5/2014 | Goodwin ............ | A61B 17/842 606/281 |
| 2014/0155906 A1 * | 6/2014 | Pratt ................... | A61B 17/8869 606/103 |
| 2015/0127003 A1 * | 5/2015 | Songer ................ | A61B 17/82 606/74 |
| 2015/0313656 A1 * | 11/2015 | Hulliger .............. | A61B 17/823 606/74 |
| 2015/0342657 A1 * | 12/2015 | Voisard ............... | A61B 17/823 606/103 |

FOREIGN PATENT DOCUMENTS

| | | |
|---|---|---|
| DE | 4021246 | 1/1992 |
| DE | 4024334 | 2/1992 |
| DE | 4200757 | 7/1992 |
| DE | 4127550 | 2/1993 |
| DE | 4314185 | 11/1993 |
| DE | 19716504 | 12/1998 |
| DE | 19806628 | 8/1999 |
| EP | 0009327 | 4/1980 |
| EP | 0201905 | 11/1986 |
| EP | 0299387 A1 | 1/1989 |
| EP | 0512297 | 11/1992 |

(56) References Cited

FOREIGN PATENT DOCUMENTS

| | | |
|---|---|---|
| EP | 0597257 A2 | 5/1994 |
| EP | 0608592 | 8/1994 |
| EP | 0780096 | 6/1997 |
| EP | 0876798 | 11/1998 |
| EP | 0587635 B1 | 3/1999 |
| EP | 0937930 | 8/1999 |
| EP | 0858419 B1 | 7/2000 |
| EP | 1564144 A2 | 8/2005 |
| FR | 2381603 A1 | 9/1978 |
| FR | 2677536 | 12/1992 |
| FR | 2690727 | 11/1993 |
| FR | 2702951 | 9/1994 |
| FR | 2906704 | 4/2008 |
| GB | 2266557 | 11/1993 |
| GB | 2414936 | 12/2005 |
| JP | 2004298501 | 10/2004 |
| WO | WO 88/06022 | 8/1988 |
| WO | WO 2006/062419 | 6/2006 |
| WO | WO 2006/136938 | 12/2006 |
| WO | WO 2009/013397 | 1/2009 |
| WO | WO 2009/091313 | 7/2009 |
| WO | WO 2010/041101 | 4/2010 |
| WO | WO 2010/108050 A2 | 9/2010 |

\* cited by examiner

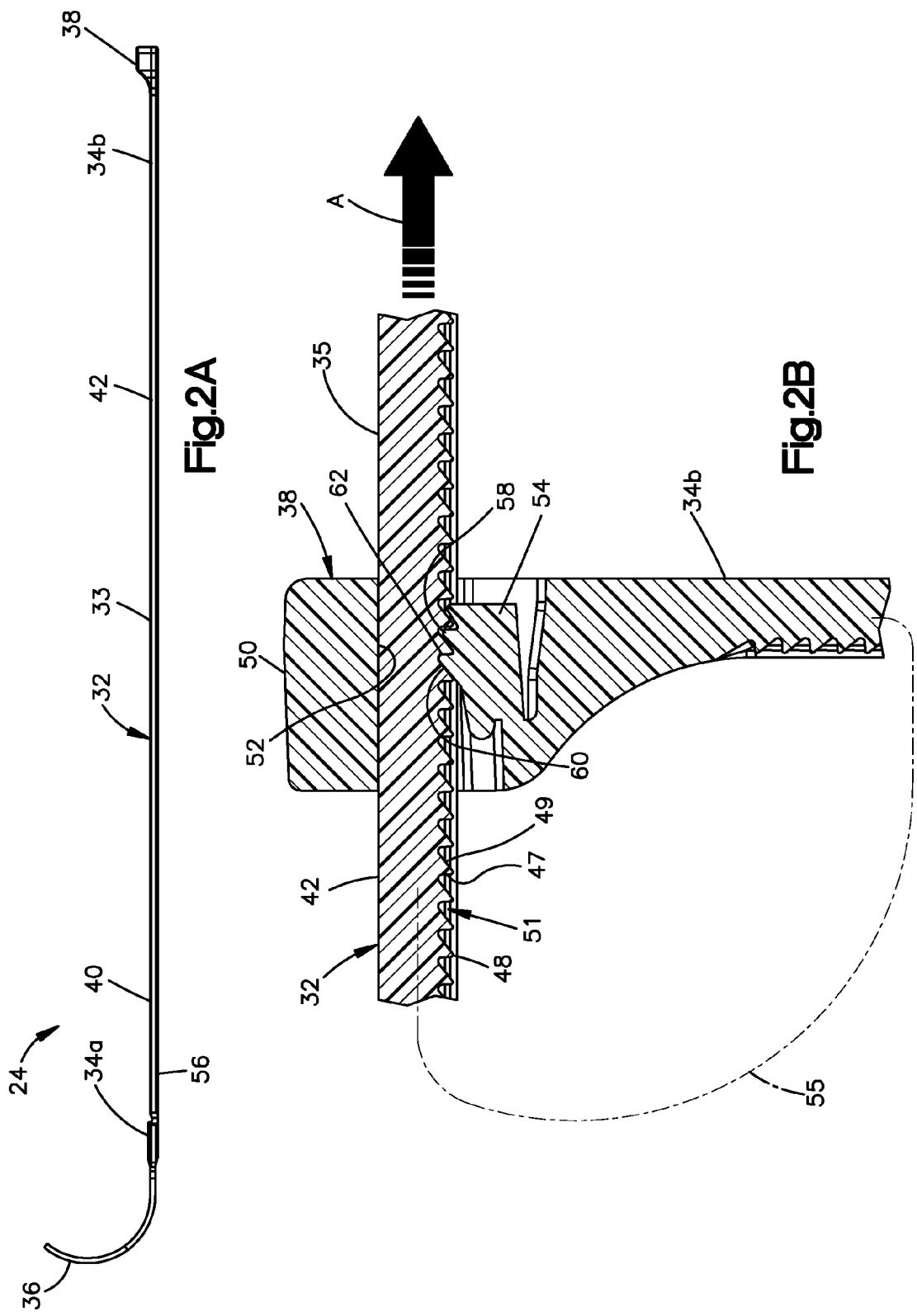

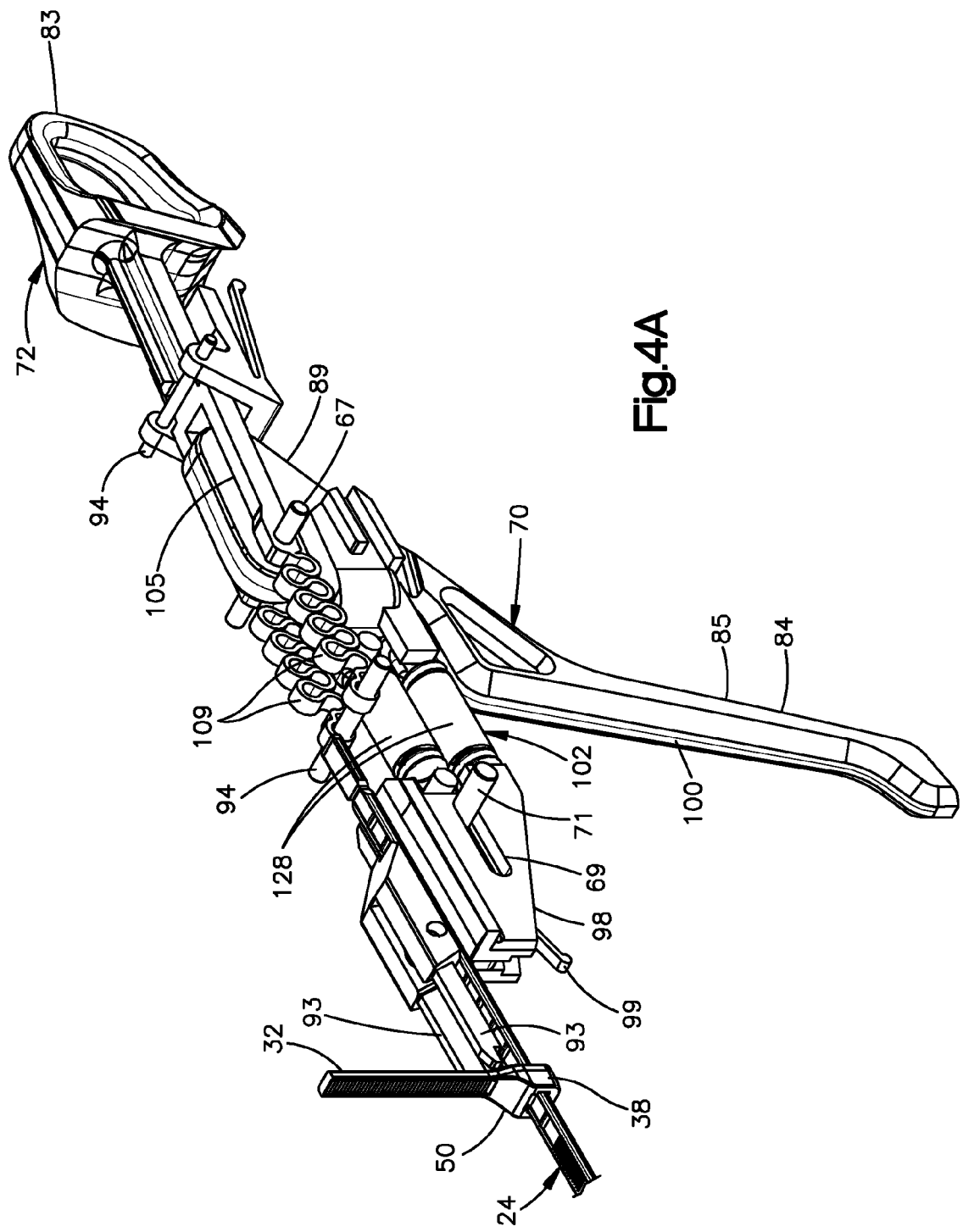

BONE FIXATION ASSEMBLY

CROSS-REFERENCE TO RELATED APPLICATIONS

This claims the benefit of U.S. Patent Application Ser. No. 62/005,552 filed May 30, 2014, the disclosure of which is hereby incorporated by reference as if set forth in its entirety herein.

BACKGROUND

In order to provide access to certain internal anatomy, such as the heart during an open heart procedure, midline sternotomies are typically performed. A midline sternotomy creates a cut substantially along the midline of the sternum, thereby dividing the ribcage into two halves and allowing the surgeon to move the ribcage so as to provide access to the heart. Upon completion of the open heart procedure, it is desired to approximate and compress the sternum, and rigidly maintain the sternal halves in their approximated position relative to each other so that the sterna halves are restricted from moving with respect to each other to promote bone fusion in the weeks following the surgical procedure.

During normal anatomical function, for instance during respiration, body movement, and carrying of objects, forces can be generated that act on the sternum. One conventional system sternal fixation assembly includes stainless steel wires that are placed either parasternally (around the sternum) or transsternally (through the sternum bone) using a cutting needle that is attached to the wire, and subsequently twisted to tighten the wire against the sternum. However, the twisting generates tensile forces onto the wires that tend to weaken the wire, which can result in breakage both during the closure or post-operatively. Furthermore, this type of system relies on the experience of the surgeon when tightening the wires. If the wires are not tightened enough, the sternal compression can be compromised. If the wires are tightened too much, the wire can cut into or through the sternum and/or can break.

SUMMARY

In accordance with one embodiment, a bone fixation instrument has a front end and a rear end spaced from the front end in a rearward direction. The bone fixation instrument can be configured to apply tension to a bone fixation member so as to tighten the bone fixation member about a target bone. The bone fixation instrument can include a grip configured to attach to a free end of the bone fixation member. The bone fixation instrument can further include a traveler that supports the grip such that as the traveler moves in the rearward direction, the grip moves along with the traveler in the rearward direction so as to increase tension in the bone fixation member when the grip is attached to the bone fixation member. The bone fixation instrument can further include a cutter arm that carries a cutter blade and is configured to move the cutter blade to a cutting position whereby the cutter blade severs the free end of the bone fixation member when the grip is attached to the bone fixation member. The bone fixation instrument can further include an actuator configured to be selectively independently coupled to the traveler and the cutter arm. The bone fixation instrument can further include a toggle member that is movable between a first and a second position. When the toggle member is in the first position, the bone fixation instrument can be in a tensioning mode whereby movement of the actuator causes the traveler to move in the rearward direction thereby increasing the tension in the bone fixation member when the grip is attached to the bone fixation member. When the toggle member is in the second position, the bone fixation instrument can be in a cutting mode whereby movement of the actuator causes the cutter arm to move the cutter blade to the cutting position.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

FIG. 2A is a perspective view of the bone fixation member illustrated in FIG. 1, including a body and a locking member, showing the bone fixation member in an initial configuration;

FIG. 2B is an enlarged perspective view of a portion of the bone fixation member illustrated in FIG. 2A, showing the body inserted through the locking member so as to secure the bone fixation member about an underlying bone;

FIG. 4A is a perspective view of the bone fixation instrument illustrated in FIG. 1, with portions removed to illustrate internal components including a tension assembly and a cutter assembly;

DETAILED DESCRIPTION

Figure 1:
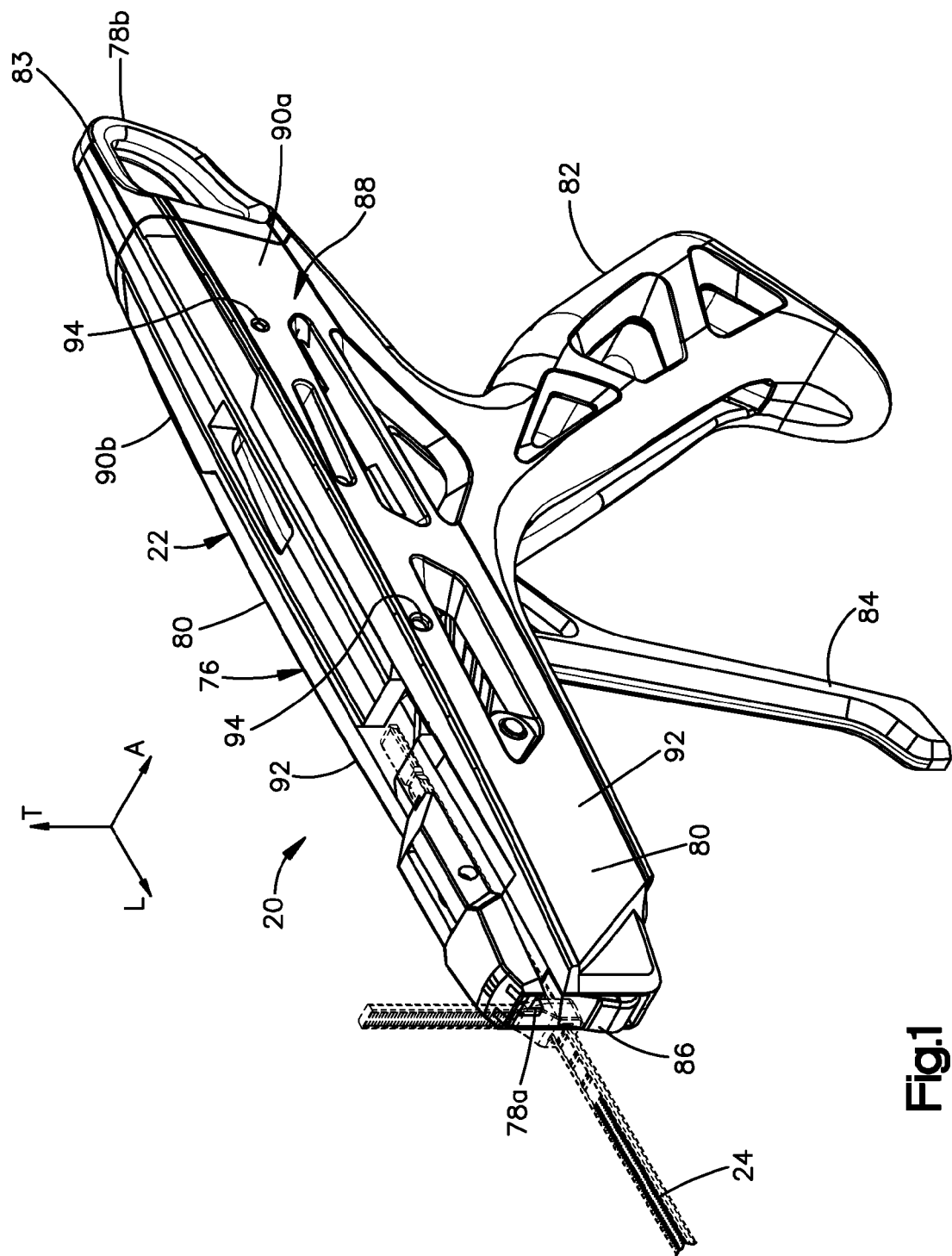
FIG. 1 is a perspective view of a bone fixation assembly constructed in accordance with one embodiment, including a bone fixation instrument and a bone fixation member received by the bone fixation member.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIGS. 1-3B generally, a bone fixation assembly 20 includes a bone fixation instrument 22 and at least one bone fixation member 24 such as a plurality of bone fixation members 24 that are configured to secure a first and second bone segments 26a and 26b of a target bone 28, such as a sternum, that are separated at a fracture location 30 together in a compressed approximated position.

In accordance with the illustrated embodiment, each bone fixation member 24 can be substantially configured as a cable tie, and can include a flexible strap 32 defines a strap body 33 and has first end 34a and a second end 34b opposite the first end 34a along the length of the strap 32, a needle tip 36 that extends from the first end 34a, and a locking mechanism 38 that extends from the second end 34b. The strap 32 can be made from any suitable biocompatible material as desired, such as PEEK.

Each bone fixation member 24 can further include a first initiation region 40 that extends from the first end 34a toward the second end 34b along a portion of a length of the strap 32 (for instance, approximately ⅓ the length of the strap 32) and a second locking region 42 that extends between the first initiation region 40 and the second end 34b. In accordance with the illustrated embodiment, the second locking region 42 extends from the first initiation region 40 to the second end 34b. The first initiation region 40 can include a plurality of small protrusions that extend out from the strap body 33 and alternate with recessed regions disposed between adjacent protrusions. Alternatively, the initiation region 40 can be substantially smooth and devoid of protrusions or teeth. The second locking region 42 can include a plurality of locking teeth 48 that extend out from the strap body 33 a distance greater than the protrusions and are separated by recessed regions 51 disposed between adjacent locking teeth. It should be appreciated that the locking region 42 can extend along any portion up to all of the strap body 33 as desired. The locking teeth 48 can extend out from one side of the strap body 33 or both opposed sides of the strap body 33 as desired.

The locking mechanism 38 includes a housing 50 a strap receiving slot 52 that extends through the housing 50 and is configured to receive the first end 34a of the strap 32. In accordance with the illustrated embodiment, the first end 34a is inserted through the slot 52 so as to define a loop 55 about the target bone 28. The locking mechanism 38 is configured to allow the strap 32 to translate unidirectionally through the slot 52 along the direction of Arrow A so as to reduce the size of the loop 55 about the first and second segments 26a and 26b of the target bone 28. For instance, the needle tip 36 can be inserted through the slot 52 and subsequently removed, for instance by cutting a neck 56 of the strap body 33 that defines reduced thickness at a location adjacent the needle tip 36, such that the strap 32 remains in the slot 52. In accordance with the illustrated embodiment, the locking mechanism 38 includes a locking member such as a tongue 54 that is connected to the housing 50 and includes at least one complementary tooth such as a plurality of locking teeth 58 that extend into the slot 52. The locking teeth 58 define a beveled leading edge 60 that that is configured to cam over complementary beveled leading edges 49 of the locking teeth 48 when the strap 32 is translated through the slot 52 along the direction of Arrow A. The locking teeth 58 and 48 further define trailing edges 62 and 47 that are sloped less than the beveled leading edges 60, such that the trailing edges 62 and 47 engage to prevent the strap 32 from translating through the slot 52 along the direction opposite Arrow A, which would increase the size of the loop 55.

During operation, the strap 32 is wrapped around the first and second segments 26a and 26b of the target bone 28, and the needle tip 36 is inserted through the slot 52 and pulled through the slot 52 so as to cause the strap 32 to subsequently translate through the slot 52. The needle tip 36 can be removed from the strap 32, and the strap 32 can then be further pulled, for instance manually, through the slot 52. As the strap 32 is translated through the locking mechanism 38 along the direction of Arrow A, the small protrusions of the initiation region 40 can slide through the slot 52 without engaging the locking teeth 58 of the locking mechanism 38. As the locking region 42 of the strap 32 is translated through the slot 52 along the direction of Arrow A, the locking teeth 48 and 58 can engage to prevent the tension that is induced in the strap 32 from causing the strap 32 to back out of the slot 52 along a direction opposite Arrow A. For instance, as the strap 32 translates through the locking mechanism 38 along the direction of Arrow A, the size of the loop 55 about the target bone 28 decreases until tactile feedback indicates that tension has been induced in the strap 32.

Figure 3A:
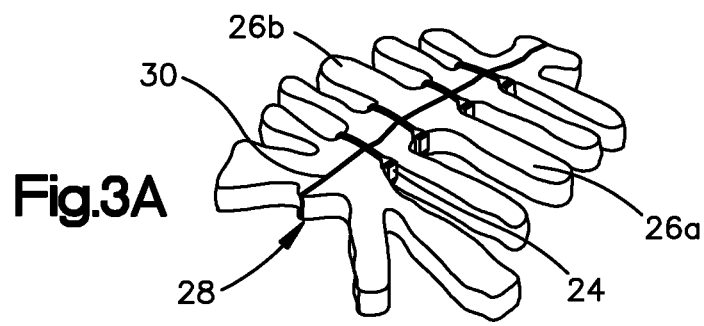
FIG. 3A is a perspective view of a plurality of the bone fixation members illustrated in FIG. 2A shown tightened about a target bone and cut.
Figure 3B:
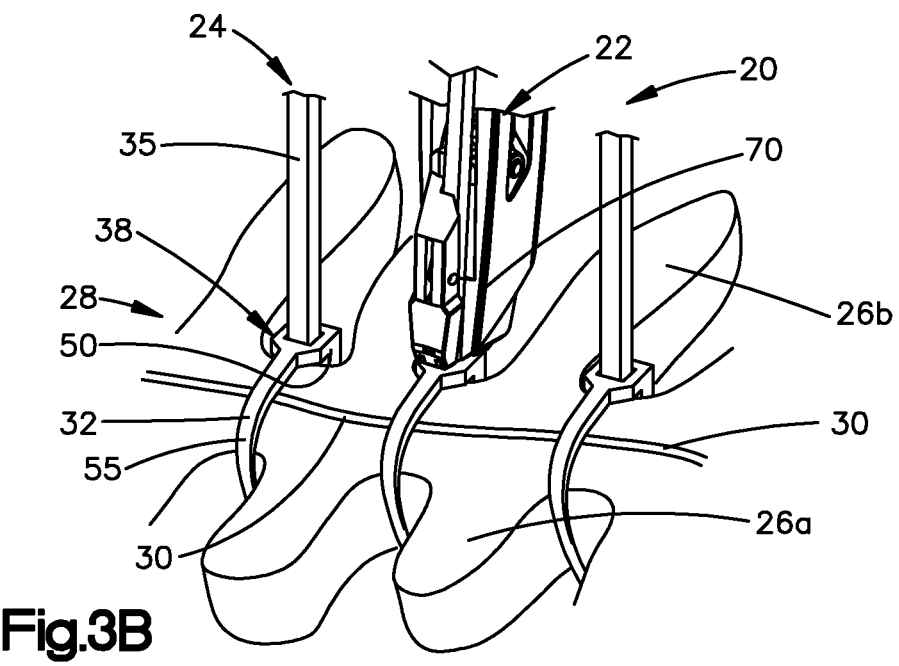
FIG. 3B is a perspective view of the bone fixation instrument illustrated in FIG. 1 operatively coupled to and tightening one of a plurality of the bone fixation members illustrated in FIG. 3A.
Figure 3C:
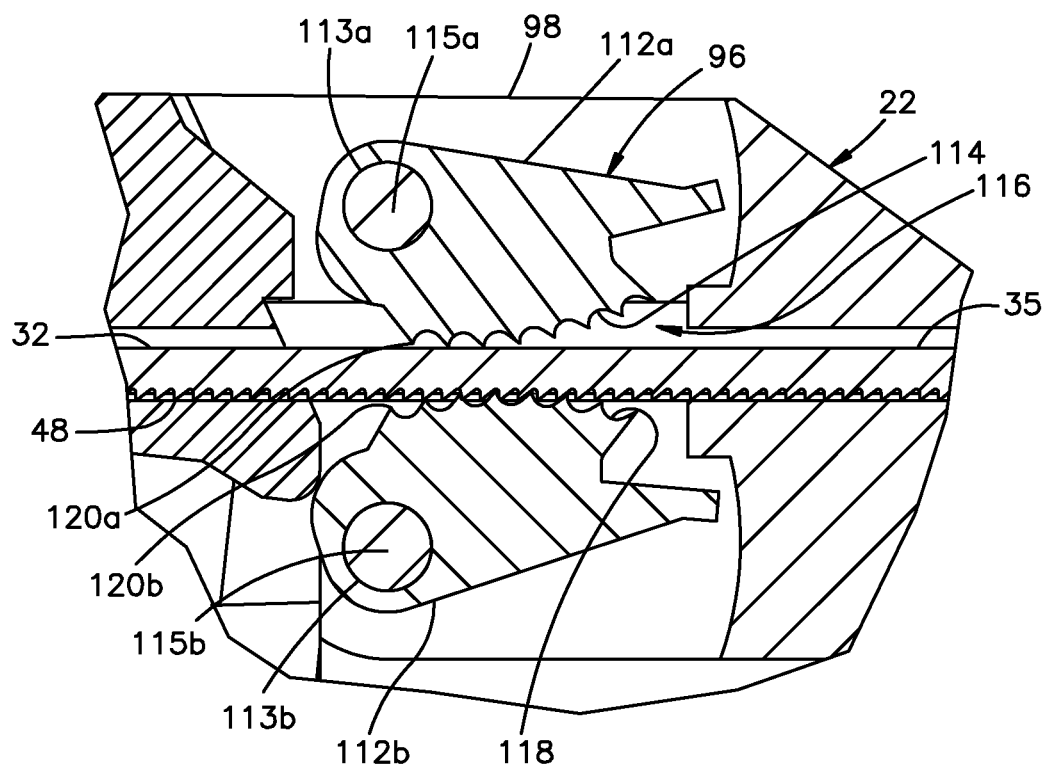
FIG. 3C is an enlarged sectional side elevation view of a grip of the bone fixation instrument as illustrated in FIG. 3B, shown receiving a free end of the bone fixation member.

As illustrated in FIG. 3B, the fixation instrument 22 includes a tension assembly 70 that is configured to secure the fixation instrument 22 to the strap 32, and is further configured to further pull the strap 32 through the locking mechanism 38 thereby further inducing tension in the strap 32 until the strap 32 has securely compressed the bone first and second bone segments 26a and 26b of the target bone 28 together at the fracture location 30. As illustrated in FIG. 3C, and as described in more detail below, the tension assembly 70 includes a traveler 98 and a grip 96 configured to be secured to the free end 35 of the strap 32. The grip 96 is further coupled to the traveler 98 such that movement of the traveler causes movement of the grip 96. Thus, when the fixation instrument 22 abuts the housing 50, and the traveler 98 moves away from the housing 50, the grip 96 likewise moves away from the housing 50, thereby inducing tension in the strap 32.

The grip 96 can include a first upper grip member 112a and a second lower grip member 112b spaced from the upper grip member 112a so as to define a gap 116 disposed between the upper and lower grip members 112a and 112b. The upper grip member 112a defines a first grip surface 114 that faces the lower grip member 112b, and can further define a plurality of teeth 120a that extend out from the first grip surface 114 toward the lower grip member 112b. The teeth 120a are configured to assist in reliably securing the grip 96 to the strap 32. For instance, the teeth 120a can interlock with complementary teeth 48 of the strap 32. The lower grip member 112b defines a second grip surface 118 that faces the first grip surface 114. The lower grip member 112b can further define a plurality of teeth 120b that extend out from the second grip surface 118 toward the upper grip member 112a. The teeth 120b are configured to assist in reliably securing the grip 96 to the strap 32. For instance, the teeth 120a can interlock with complementary teeth of the strap 32. Thus, it should be appreciated that the grip 96 is configured to engage the free end 35 of the strap 32 whether the strap 32 is oriented such that the teeth of the strap 32 face up or down. The first and second grip surfaces 114 and 118 can be sized and shaped as desired. In accordance with the illustrated embodiment, the first and second grip surfaces 114 and 118 are curved and substantially arc-shaped in accordance with the illustrated embodiment, such that the first and second grip surfaces 114 and 118 are convex with respect to the gap 116.

The upper grip member 112a and the lower grip member 112a can be coupled to the traveler 98 as described above. For instance, the upper grip member 112a can be pivotally coupled to the traveler 98 at a first grip pivot location 113a about a first grip pivot pin 115a that defines a first grip pivot axis. The grip 96 can further include a biasing member such as a torsion spring that biases the upper grip member 112a to pivot about the first grip pivot location 113a so as to bias the teeth 120a toward the gap 116. In particular, the first grip surface 114 can extend eccentrically about the first grip pivot location 113a such that the grip surface 114 moves toward the gap 116 under the force of the torsion spring. Similarly, the lower grip member 112b can be pivotally coupled to the traveler 98 at a second grip pivot location 113b about a second grip pivot pin 115b that defines a second grip pivot axis. The grip 96 can further include a biasing member such as a torsion spring that biases the lower grip member 112b to pivot about the second grip pivot location 113b so as to bias the teeth 120b toward the gap 116. In particular, the second grip surface 118 can extend eccentrically about the second grip pivot location 113b such that the second grip surface 118 moves toward the gap 116 under the force of the torsion spring.

Thus, during operation, the gap 116 receives the free end 35 of the strap 32, such that the teeth 48 of the free end 35 face one or both of the upper and lower grip members 112a and 112b. As the free end 35 is received in the gap 116, the upper and lower grip members 112a and 112b pivot about their respective pivot axes, such that the first and second grip surfaces 115 and 118 move away from each other against the force of the respective torsion springs. The torsion springs thus bias the teeth 120a and 120b against the free end 35. The teeth can be oriented such that the teeth 120a and 120b are configured to ratchet over the teeth 48 of the free end 35 as the free end 35 is inserted into the gap 116 in a rearward direction. Subsequent movement of the traveler 98 in the rearward direction relative to the housing 50 of the locking mechanism 38 causes one or both of the teeth 120a and 120b to engage the teeth 48 and bias the free end 35 to move in the rearward direction relative to the housing 50, thereby inducing tension in the strap 32. While each of the grip members 112a and 112b can carry respective teeth, it should be appreciated in one example that only one of the grip members 112a and 112b can carry teeth, such that the free end 35 of the strap 32 engages the grip 96 only in a predetermined orientation.

Figure 3D:
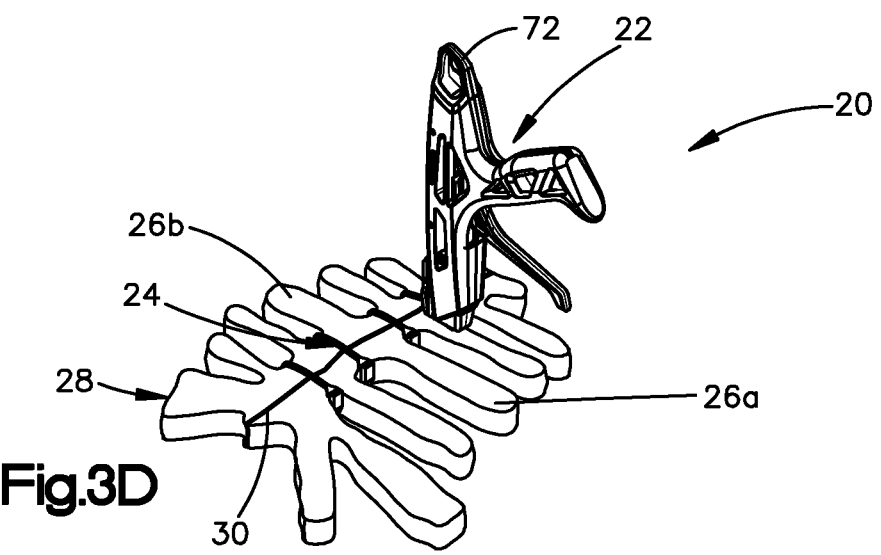
FIG. 3D is a perspective view of the bone fixation instrument illustrated in FIG. 1 operatively coupled to and cutting one of the tightened bone fixation members illustrated in FIG. 3B.

As illustrated in FIG. 3D, the fixation instrument 22 further includes a cutter assembly 72 that is configured to cut a free end 35 of the strap 32 that has passed through the locking mechanism 38 once a desired tension has been induced in the strap 32 about the first and second segments 26a and 26b of the target bone 28. For instance, the desired tension can be within a range defined by and between a lower end that can be approximately 50 Newtons or approximately 80 Newtons, and an upper end that can be approximately 150-160 Newtons or 200 Newtons. It should be appreciated that the desired tension can depend on the bone quality and the preference of the surgeon, and can for instance be any tension as desired that reliably secures the target bone 28 without overtightening the strap 32.

Figure 4B:
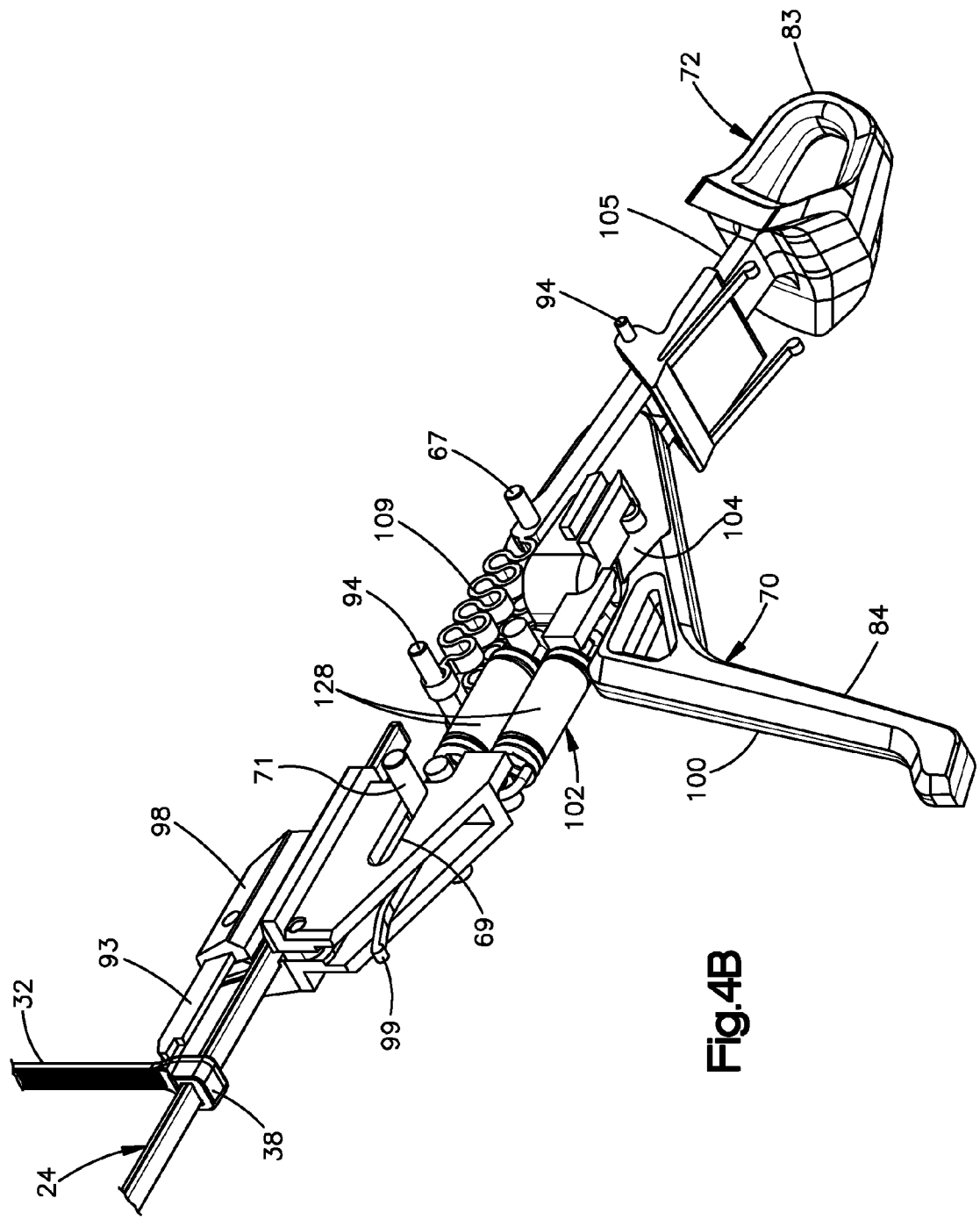
FIG. 4B is a another perspective view of the bone fixation instrument illustrated in FIG. 4A.

Referring now to FIGS. 1 and 4A-4B, the fixation instrument 22 includes a body 76 that defines a front end 78a and an opposed rear end 78b spaced from the front end 78a along a longitudinal direction L and opposed sides 80 that are spaced along a lateral direction A that is substantially perpendicular with respect to the longitudinal direction L. The front end 78a is spaced from the rear end 78b in a forward direction, and the rear end 78b is spaced from the front end 78a in a rearward direction opposite the forward direction. The fixation instrument 22 further includes a handle 82 that is supported by the body 76, and can extend down from the body 76 substantially along a transverse T direction that is substantially perpendicular with respect to both the longitudinal direction L and the lateral direction A. In accordance with the illustrated embodiment, the transverse direction T is oriented vertically, and the longitudinal and lateral directions L and A are oriented horizontally, though it should be appreciated that the orientation of the fixation instrument may vary during use. In accordance with the illustrated embodiment, the body 76 is elongate in the longitudinal direction L.

The fixation instrument 22 further includes an actuator, such as a trigger 84, that extends down from the body 76 at a location spaced forward from the handle 82, and a nose 86 disposed at the front end 78a of the body 76. The fixation instrument 22 can further include a toggle member 83 that extends rearward from the rear end 78b of the body 76. As will be described in more detail below, actuation of the toggle member 83 can cause the fixation instrument 22 to iterate from a tensioning mode to a cutting mode. The handle 82, the trigger 84, and the nose 86 can be discreetly attached to the body 76 or integral and monolithic with the body 76 as desired. The body 76 can include an outer housing 88 that includes a pair of housing members 90a and 90b that are laterally opposed and define respective outer sides 92 and can be joined together via fasteners 94 such as dowels or screws or the like or any suitable alternative attachment mechanism so as to support the various internal components of the fixation instrument 22 as described below.

The housing 80 can support the tension assembly 70 that is configured to inducing tension in the strap 32 as described above. The housing 88 is further configured to support the cutter assembly 72 that is configured to remove the free end 35 of the strap 32 once the tension assembly 70 has induced a desired level of tension in the strap 32. The traveler 98 is movable relative to the body 76. As described above, the traveler 98 supports the grip 96, such that movement of the traveler 98 in the rearward direction relative to the body 76 likewise causes the grip 96 to move in the rearward direction relative to the body 76. Accordingly, when the nose 86 of the body 76 is braced against the housing 50 and the grip 96 is attached to the strap 32, movement of the traveler in the rearward direction relative to the housing 50 induces tension in the strap 32.

The tension assembly 70 can further include an actuator 100 such as the trigger 84 and a tension limiter 102 connected between the trigger 84 and the traveler 98. The tension assembly 70 can further include a force transfer member 104 (see FIG. 5B) that is configured to be selectively coupled between the trigger 84 and the tension limiter 102, thereby operatively coupling the trigger 84 to the traveler 98. For instance, the tension limiter 102 can be connected to the traveler 98 and the force transfer member 104. The force transfer member 104 is thus attached to the tension limiter 102 at a first location, and is configured to be selectively coupled to the trigger 84 at a second location. The cutting assembly 72 includes a cutter arm 106 that is movably supported by the body 76 and a cutter blade 108 that is carried by the cutter arm 106 (see FIG. 5C). The cutter arm 106 is movable from a disengaged configuration (see FIG. 5C) whereby the cutter blade 108 is spaced from the free end 35 of the strap 32 that is received in the grip 96 to a cutting configuration (see FIG. 8A) whereby the cutter blade 108 is in a cutting position so as to cut through the free end 35 of the strap 32. For instance, the cutter blade 108 can cut through the free end 35 of the strap 32 along the transverse direction T.

The fixation instrument 22 is operable in a tensioning mode whereby the trigger 84 is coupled to the force transfer member 104, such that actuation of the trigger 84 urges the force transfer member 104 to move rearwardly. The fixation instrument 22 is further operable in a cutting mode whereby the trigger 84 is coupled to the cutter arm 106, such that actuation of the trigger 84 urges the cutter arm to move from the disengaged configuration to the cutting configuration. It should be appreciated that when the fixation instrument 22 is in the tensioning mode, the trigger 84 is decoupled from the cutter arm 106. Accordingly, actuation of the trigger 84 does not move the cutter arm 106 to the cutting configuration. Similarly, when the fixation instrument 22 is in the cutting mode, the trigger 84 is decoupled from the force transfer member 104, and thus the traveler 98. Accordingly, actuation of the trigger 84 does not cause the traveler 98 to move rearwardly. The fixation instrument 22 can be placed in the tensioning mode when the toggle member 83 is in an initial position (see FIGS. 4A-4B). The fixation instrument can be placed in the cutting mode when the toggle member 83 is in an armed position (see FIGS. 7A-7D). it should thus be appreciated that the trigger 84 is configured to be selectively independently coupled to the traveler 98 and the cutter arm 106.

During operation, with further reference to FIG. 3C, while the fixation instrument 22 is in the tensioning mode, the free end 35 of the strap 32 is received in the grip 96, the nose 86 is placed against the housing 50 of the locking mechanism 38, and the actuator 100 is moved from an first initial position to a second actuated position that causes the traveler 98 to move rearward, thereby inducing tension in the strap 32 when the tension in the strap 32 is less than a select tension, which can be a desired maximum tension as determined by the tension limiter 102. The fixation instrument 22 can include one or more rails 93 that are supported by the housing 88, and extend in the longitudinal direction L through corresponding apertures that extend through traveler 98 in the longitudinal direction L. Thus, the traveler 98 is configured to move along the rails 93 in the longitudinal direction L. The traveler 98 can further define a slot 69 that extends therethrough in the lateral direction A. The fixation instrument 22 can further define a guide pin 71 that is fixed to the housing 88 and extends through the slot 69. Accordingly, the slot 69 moves along the guide pin 71 as the traveler 98 moves in the longitudinal direction L. Further, the front end of the slot 69 can be defined by a stop surface 73 of the traveler 98 that is configured to abut the guide pin 71 so as to limit the permitted distance of travel of the traveler 98 in the rearward direction. When the tension in the strap 32 reaches the maximum tension as defined by the tension limiter 102, the tension limiter 102 prevents the traveler 98 from moving rearward when the actuator 100 is moved to the actuated position. The traveler 98 can be coupled to a spring arm 99 that bears against the housing 88 to provide for positional stability of the traveler 98 during operation.

The tension limiter 102 includes at least one spring member 128 coupled at its rear end to the force transfer member 104, and coupled at its front end to the traveler 98. In one example, the tension limiter 102 can include a pair of spring members 128 coupled to the force transfer member 104 and the traveler 98. The spring members 128 can be coupled to the force transfer member 104 and the traveler 98 in parallel. Alternatively, the spring members 128 can be coupled to the force transfer member 104 and the traveler 98 in series. The spring members 128 can be configured as coil springs or any suitable alternative spring as desired having a spring constant in the longitudinal direction L. As the rear ends of the spring members 128 move in the rearward direction, the spring members 128 bias the traveler 98 to likewise move in the rearward direction.

Figure 5A:
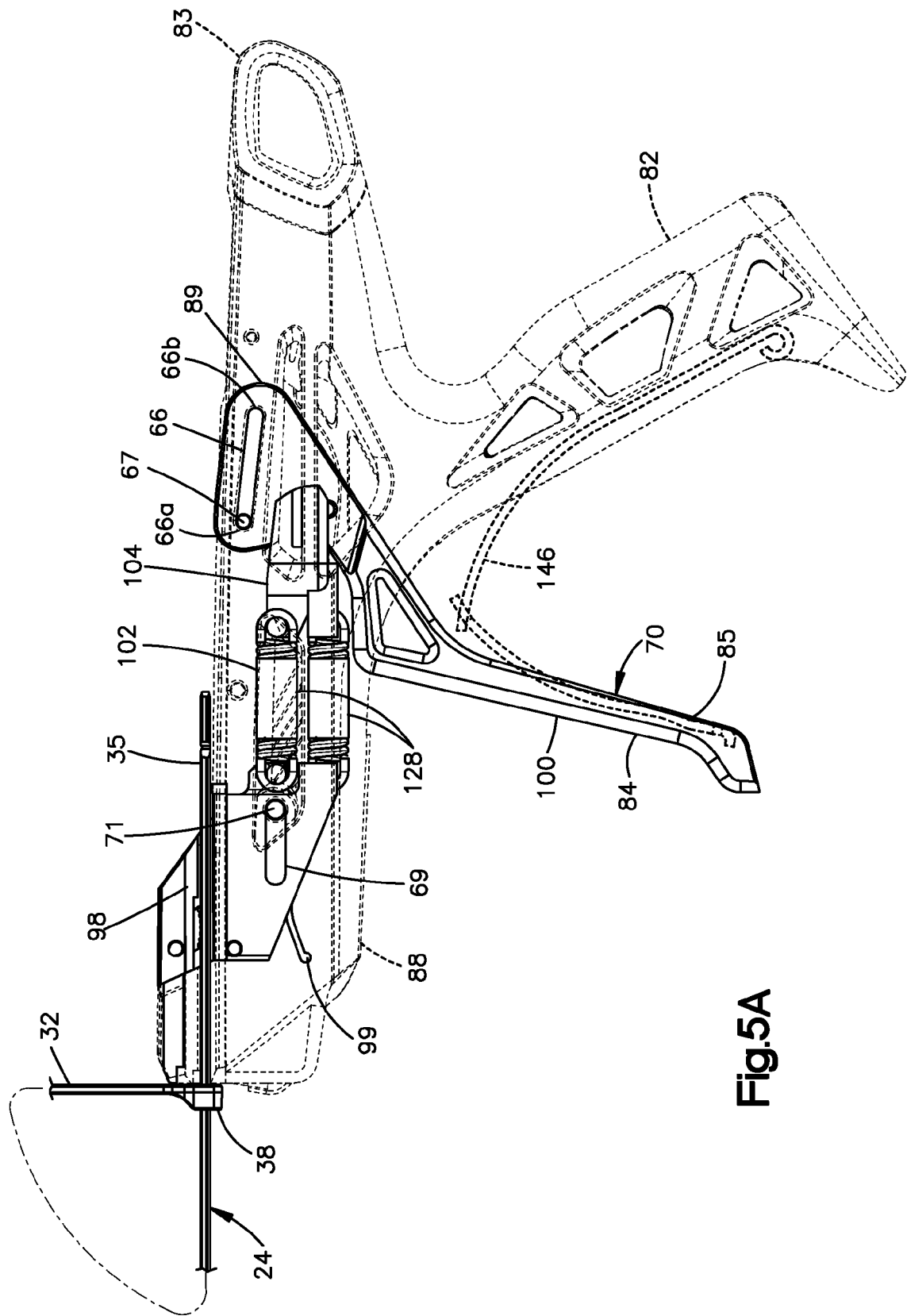
FIG. 5A is a side elevation view of the bone fixation instrument illustrated in FIG. 1, showing the tension assembly in a neutral position.
Figure 5B:
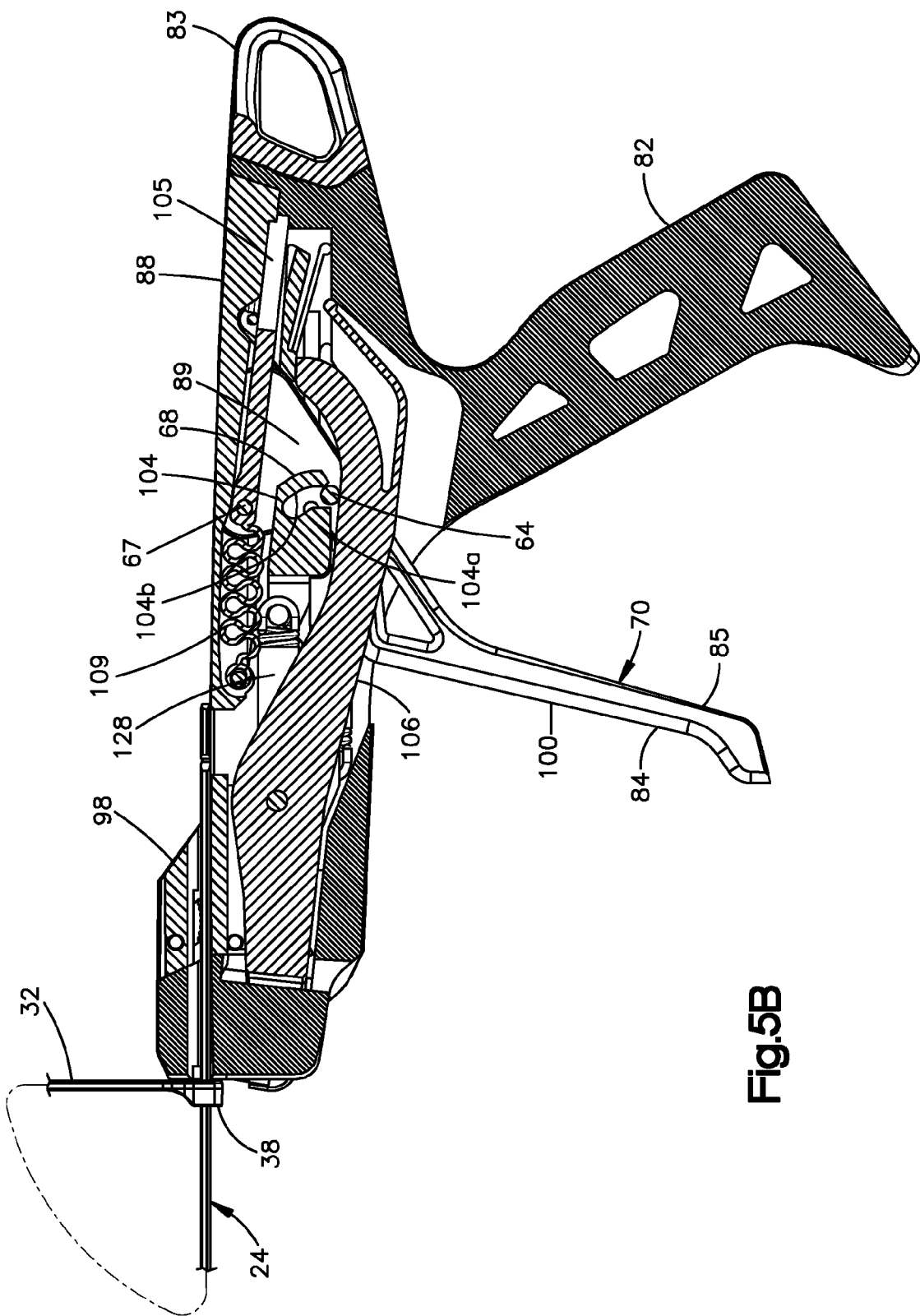
FIG. 5B is a sectional side elevation view of the bone fixation instrument as illustrated in FIG. 5A.
Figure 5C:
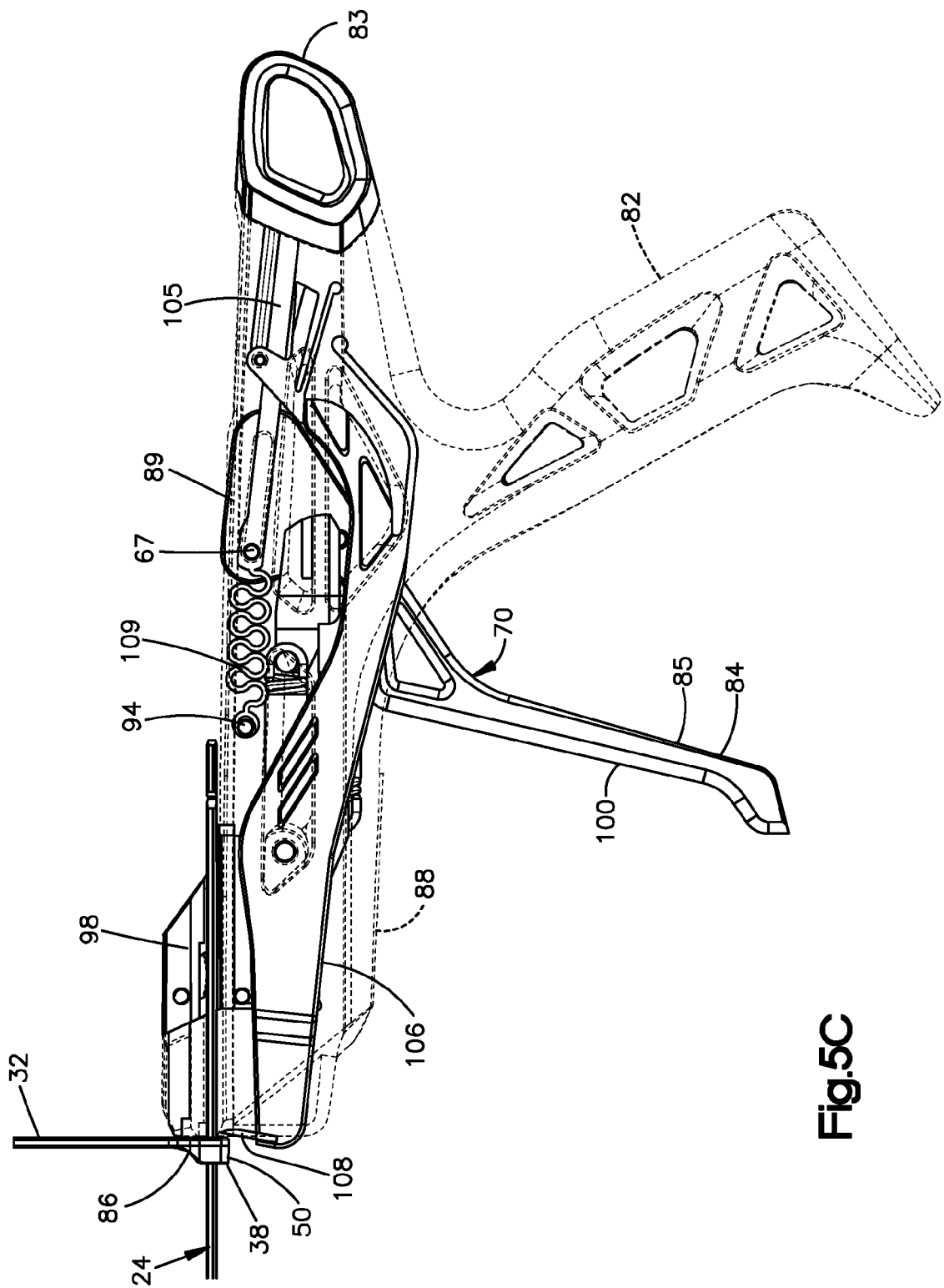
FIG. 5C is another side elevation view of the bone fixation instrument illustrated in FIG. 5A, with portions of the instrument removed for the purposes of clarity.
Figure 6A:
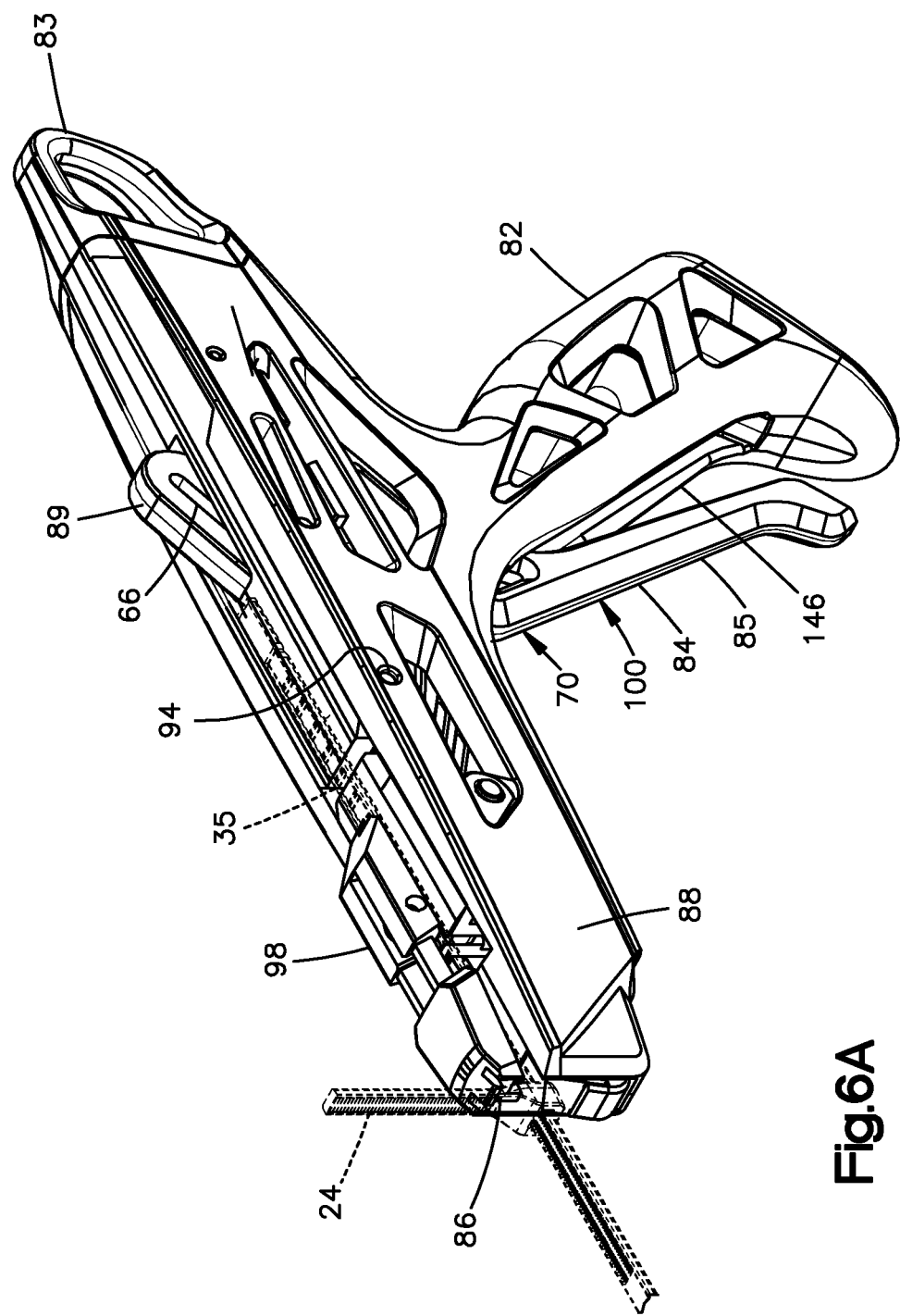
FIG. 6A is a perspective view of the bone fixation instrument illustrated in FIG. 1, showing the tension assembly in a tensioned position.
Figure 6B:
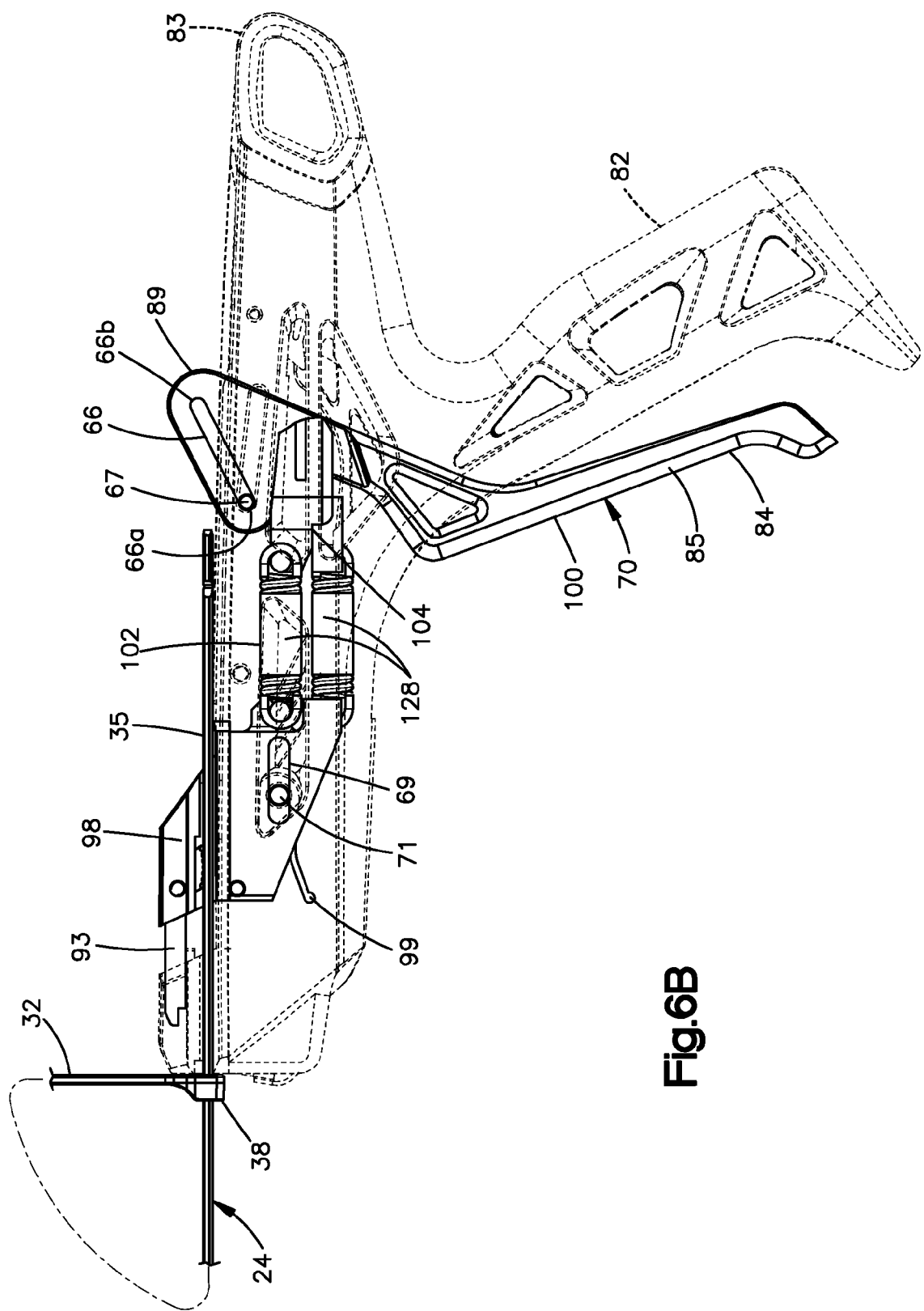
FIG. 6B is a side elevation view of the bone fixation instrument as illustrated in FIG. 6A.
Figure 6C:
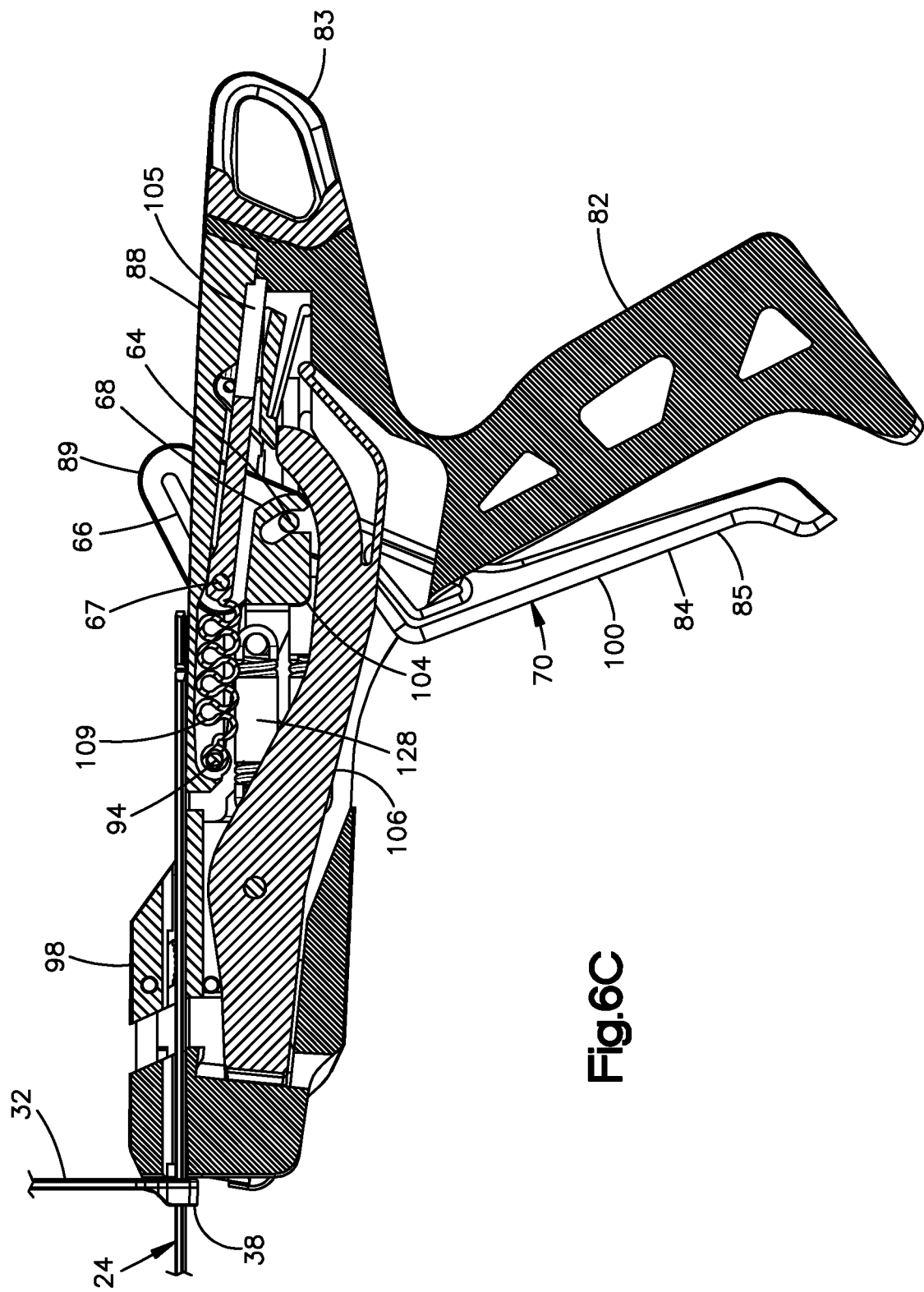
FIG. 6C is a sectional side elevation view of the bone fixation instrument as illustrated in FIG. 6A.
Figure 7A:
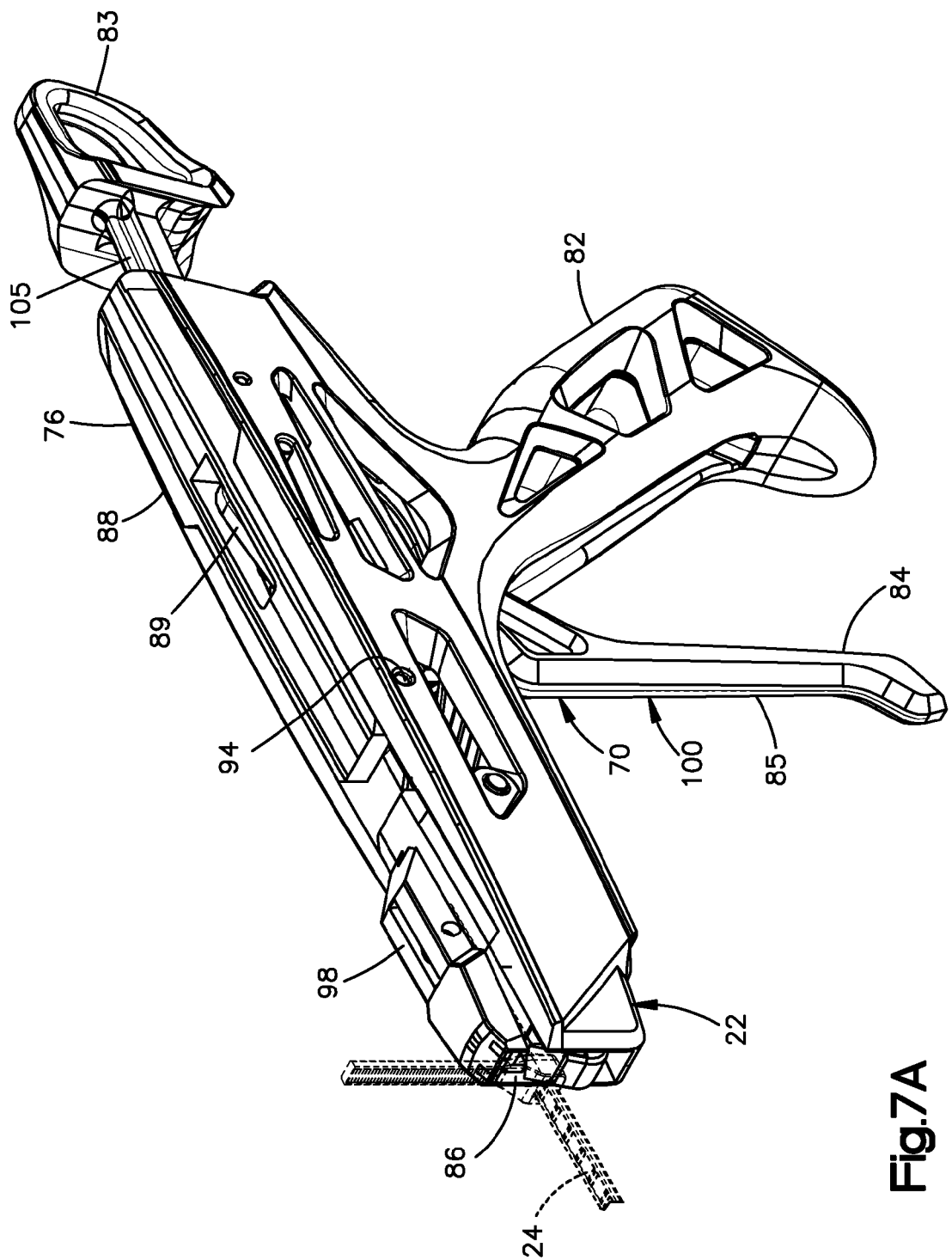
FIG. 7A is a perspective view of the front end of the bone fixation instrument illustrated in FIG. 1, shown in a cutting mode.
Figure 7B:
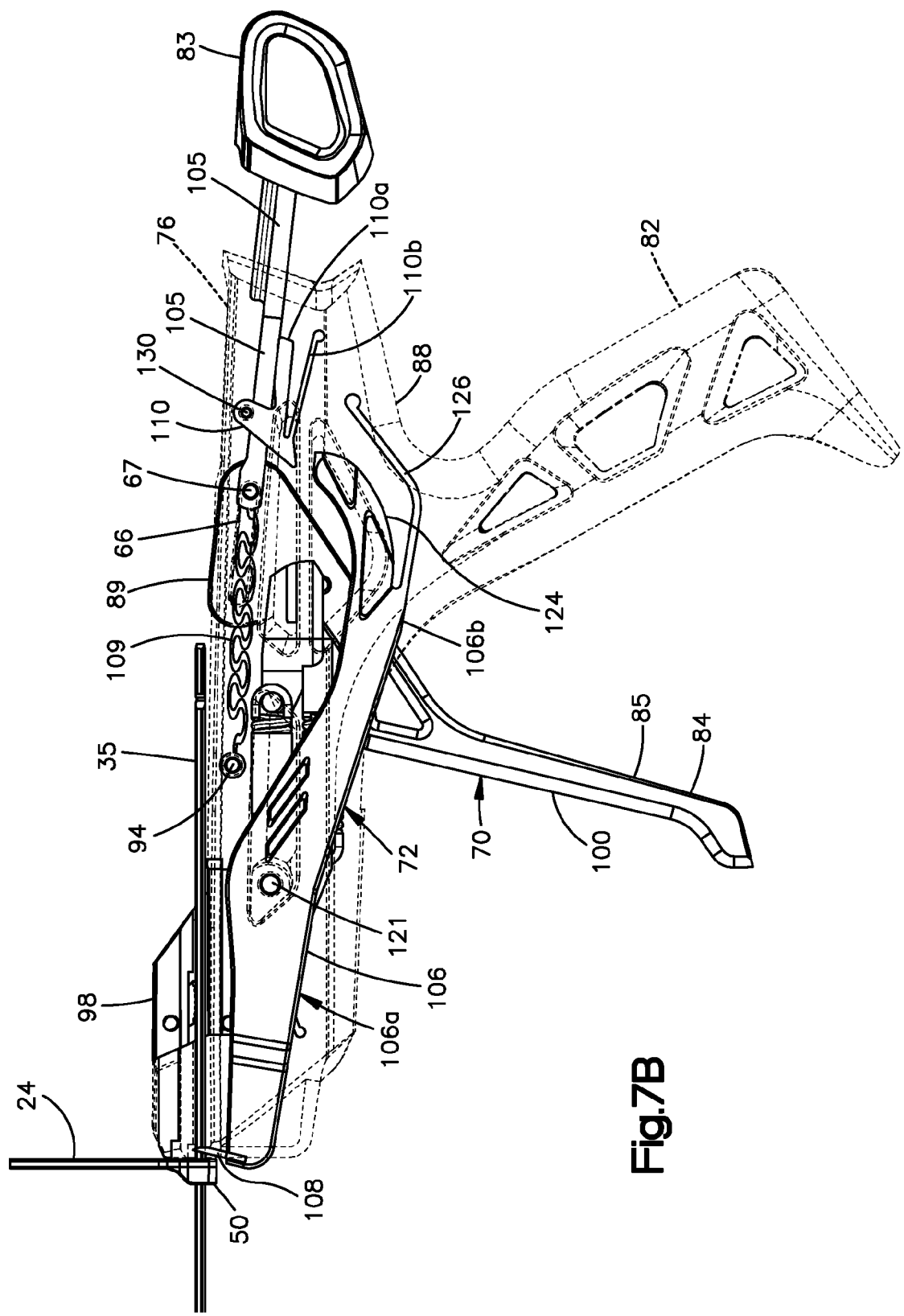
FIG. 7B is a side elevation view of the bone fixation instrument illustrated in FIG. 7A.
Figure 7C:
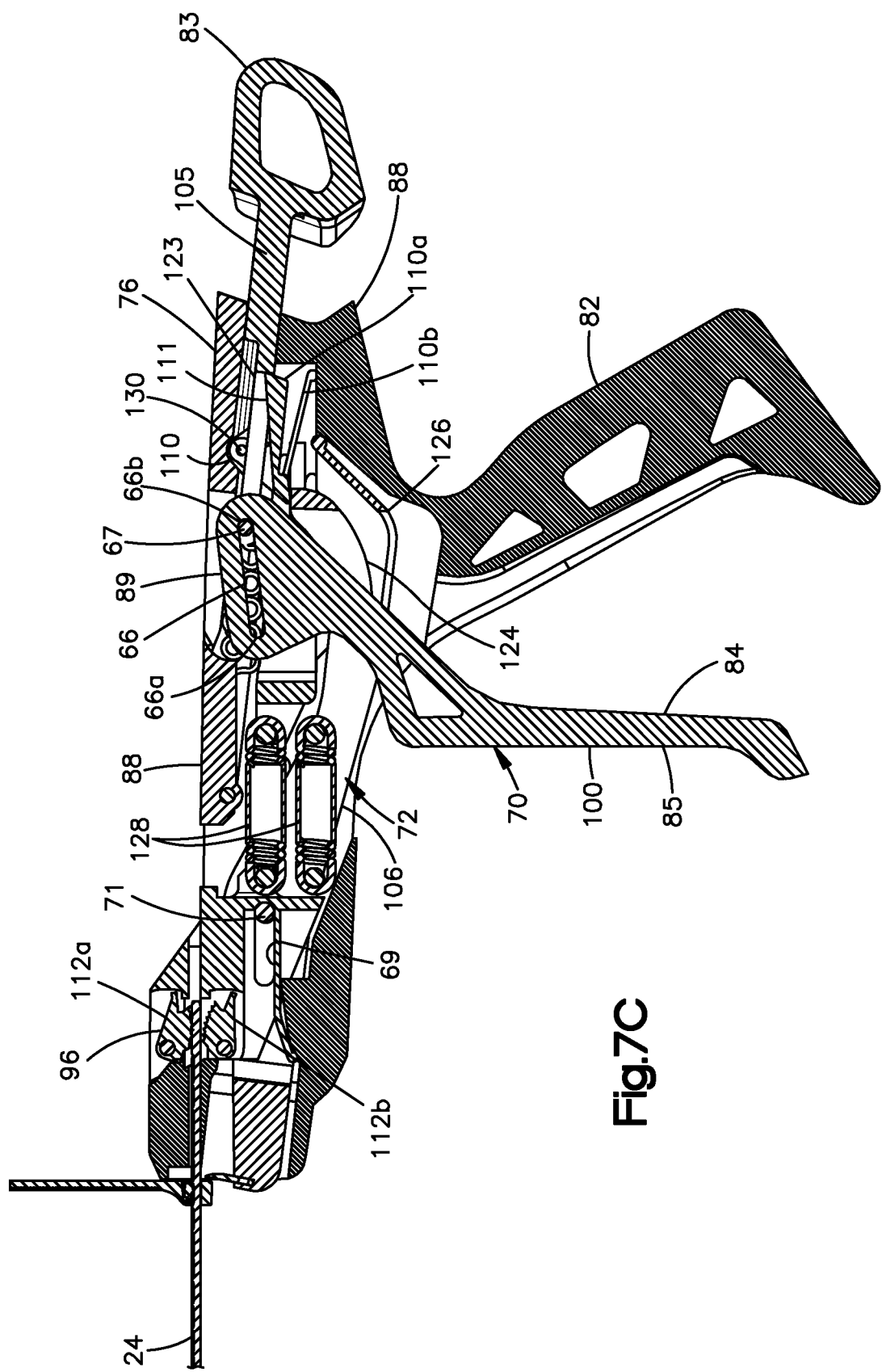
FIG. 7C is a sectional side elevation view of the bone fixation instrument illustrated in FIG. 7A.
Figure 7D:
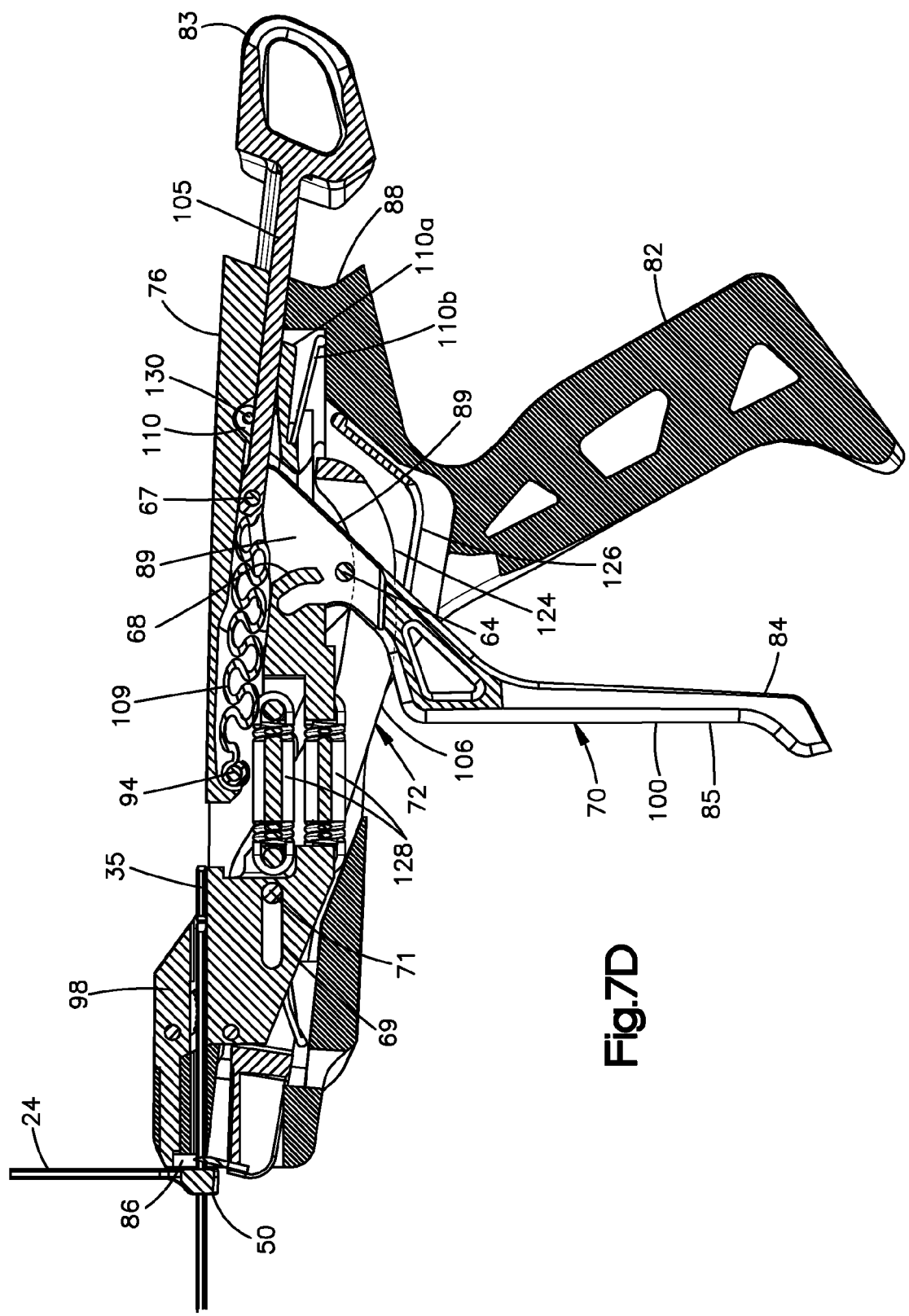
FIG. 7D is another sectional side elevation view of the bone fixation instrument illustrated in FIG. 7A.

Operation of the tension assembly 70 will now be described with further reference to FIGS. 5A-6C, whereby the fixation instrument 22 is in the tensioning mode. As illustrated in FIGS. 5A-5C, the tension assembly 70 is in a first initial or neutral configuration, whereby actuation of the trigger 84 causes a biasing force to be applied to the traveler 98 in the rearward direction. As illustrated in FIGS. 5A-5C, the trigger 84 is in a first initial or neutral position. As illustrated in FIGS. 6A-6C, the trigger 84 has been actuated from the first initial or neutral position to a second actuated position, which iterates the tension assembly 70 from the first initial or neutral configuration to the actuated configuration, whereby the biasing force is applied to the traveler 98 in the rearward direction.

Referring to FIGS. 5A-5C in particular, the trigger 84 can include a lower grip portion 85 that extends down from the housing 88 at a location spaced forward of the handle 82 and an upper securement portion 89 pivotally connected to the housing 88. In particular, the trigger 84 defines a slot 66 that extends through the upper securement portion 89 in the lateral direction A. In particular, the slot 66 can define a front end 66a and a rear end 66b that is spaced from the front end 66a in the rearward direction. The fixation instrument 22 can further define a pivot pin 67 that extends through the slot 66 in the lateral direction A. The pivot pin 67 defines a trigger pivot axis, such that the trigger 84 pivots about the trigger pivot axis as defined by the pivot pin 67 in a first pivot direction when actuated from the first position to the second actuated position. The trigger pivot axis can be oriented in the lateral direction A or any suitable alternative direction as desired. As will be appreciated below, the pivot pin 67 is movable along the longitudinal direction L. For instance, when the fixation instrument 22 is in the tensioning mode, the pivot pin 67 is disposed in a first position. When the fixation instrument is in the cutting mode, the pivot pin 67 is disposed in a second position spaced from the first position in the rearward direction. For instance, the first position can be at the front end 66a of the slot 66. The second position can be at the rear end 66b of the slot 66.

The upper securement portion 89 is further configured to be selectively coupled to and decoupled from the force transfer member 104. When the tension assembly 70 is in the tensioning mode, the upper securement portion 89 is coupled to the force transfer member 104. In particular, the trigger 84 includes an actuation pin 64 that extends out from the securement portion 89. For instance, the actuation pin 64 can extend out from the securement portion 89 along the lateral direction A. The force transfer member 104 can define a slot 68 that extends therethrough along the lateral direction A. For instance, the force transfer 104 can include a front inner surface 104a and a rear inner surface 104b that is spaced from the front inner surface 104a in the rearward direction. The front inner surfaces 104a and the rear inner surface 104b can cooperate so as to at least partially define the slot 68. The slot 68 receives the actuation pin 64 when the fixation instrument 22 is in the tensioning mode, such that the actuation pin 64 can bear against the rear inner surface 104b. When the trigger 84 is in the first position, the actuation pin 64 can be disposed at the mouth of the slot 68. The slot 68 can be arcuate in shape or can be otherwise shaped as desired. For instance, the slot 64 can be concave with respect to the forward direction.

When the fixation instrument 22 is in the tensioning mode, the pivot pin 67 is offset from the actuation pin 64 in the forward direction. Further, the actuation pin 64 is offset from the pivot pin 67 in a downward direction. Thus, referring to FIGS. 6A-6C, the user can grasp the handle 82 and the grip 85 of the trigger 84 with one hand, and squeeze the trigger 84, which causes the trigger 84 to pivot about the pivot pin 67 in a first direction such that the grip 85 travels rearward toward the handle 82. Because the actuation pin 64 is spaced rearward with respect to the pivot pin 67, movement of the trigger 84 about the pivot pin 67 to the actuated position causes the actuation pin 64 to move in the rearward and upward directions. Thus, movement of the trigger 84 to the actuated position can cause the actuation pin 64 to move further into the slot 68. Further, because the actuation pin 64 bears against the rear inner surface 104b of the force transfer member 104, movement of the actuation pin in the rearward direction urges the force transfer member 104 to likewise move in the rearward direction.

It should be appreciated that movement of the force transfer member 104 in the rearward direction causes the at least one spring member 128 to deform. For instance, the at least one spring member 128 can expand in the longitudinal direction L. Thus, the at least one spring member 128 defines a compressive force that is applied to the traveler 98 as a biasing force in the rearward direction. It should be appreciated that the at least one spring member 128, and thus the tension limiter 102, has a spring constant that is configured to apply a predetermined biasing force to the traveler 98 when the force transfer member 104 has translated rearward a distance corresponding to rearward movement of the actuation pin 64 in response to movement of the trigger 84 to the actuated position. Accordingly, so long as the tension in the loop 55 is less than a predetermined maximum tension as defined by the spring constant of the at least one spring member 128 and length of travel of the force transfer member 104, the deformation of the spring member 128 will cause the force applied by the spring member 128 to move the traveler 98 in the rearward direction. However, once the tension induced in the loop 55 reaches the predetermined maximum tension as defined by the tension limiter 102, deformation of the spring member 128 due to rearward movement of the force transfer member will cause the spring member 128 to apply a rearward biasing force against the traveler 98 that is insufficient to overcome the force necessary to move the traveler 98 in the rearward direction and further tighten the loop 55. Thus, at this point, the loop 55 will have reached its maximum predetermined tension as allowed by the fixation instrument 22.

It is recognized that after the trigger 84 has been moved to the actuated position, and the traveler 98 has moved in the rearward direction, thereby also causing the free end 35 to move in the rearward direction relative to the housing 50 of the locking mechanism 38, the tension in the loop 55 may or may not have reached the maximum predetermined tension. Whether the tension in the loop 55 is equal to the maximum predetermined tension or less than the maximum predetermined tension can be observed when actuating the trigger 84 to the actuated position. For instance, if when actuating the trigger 84 to the actuated position, the free end 35 of the strap 32 does not translate in the rearward direction or stops translating in the rearward direction, it can be determined that the tension in the loop 55 has reached the maximum predetermined tension. If, on the other hand, the free end 35 of the strap 32 translate in the rearward direction when actuating the trigger 84 to the actuated position, it can be determined that the tension in the loop 55 is less than the maximum predetermined tension.

If the tension in the loop 55 has reached the maximum predetermined tension, then the fixation instrument can be iterated from the tensioning mode to the cutting mode. If, however, the tension in the loop 55 is less than the maximum predetermined tension, then the trigger can again be moved to the actuated position. It should be appreciated that the fixation instrument can include a trigger spring member 146 (see FIG. 5A) that is connected between the handle 142 and the trigger 144 that biases the trigger 144 to pivot about the pivot pin 67 in a second pivot direction opposite the first pivot direction. Thus, after the trigger 84 has moved to the actuation position, release of the trigger 84 allows the force of the trigger spring member 146 to bias the trigger 144 to pivot about the pivot pin 67 to the first position. Alternatively, the bone fixation instrument 22 can be configured to apply sufficient tension to the loop 55 in one stoke of the trigger 144 such that the bone fixation instrument 22 can be devoid of the trigger spring member 146. It is appreciated that when the trigger 84 moves to the first position, the actuation pin 64 moves forward against the front inner surface 104a of the force transfer member 104, thereby urging the force transfer member 104 to move in the forward direction. As the force transfer member 104 moves in the forward direction, the force transfer member 104 causes the rear end of the at least one spring member 128 to move in the forward direction. Accordingly, the at least one spring member provides a biasing force that drives the traveler 98 to move in the forward direction. As the traveler 98 moves in the forward direction, the at least one of the teeth 120*a* and 120*b* that engages the teeth 48 of the strap 32 ratchets over the teeth 48. Accordingly, the traveler 98 moves along the free end 35 of the strap 32 in the forward direction. The engagement of the locking teeth 58 and 48 prevent the increased tension induced in the loop 55 from allowing the free end 35 to move through the housing in a direction opposite Arrow A that would reduce the tension in the loop 55 (see FIG. 2B).

Accordingly, once a trigger stroke has been completed whereby the trigger 84 has been moved to its actuated position as illustrated in FIG. 6A, the user can release the trigger 84 which causes the trigger spring member 146 to bias the trigger 84 to its forward position shown in FIG. 5A. Once the trigger 84 has moved to its forward position, the trigger 84 and thus the tension assembly 70 is in the first initial configuration. The trigger 84 can again be moved to the actuated position, thereby causing the traveler 98 to move in the rearward direction as described above. The trigger can be released and actuated as many times as desired until the tension in the loop 55 has reached the predetermined maximum tension as defined by the tension limiter 102.

It should appreciated that the tension limiter 102 can be configured to apply a rearward biasing force against the traveler 98 that is greater than the tension induced in the loop 55 about the target bone 28. For instance, the at least one spring member 128 can apply a force to the traveler 98 in the rearward direction that is sufficient to overcome both the tension of the loop 55 and the additional force that causes one or both of the locking teeth 48 and 58 to deflect as the teeth ride over each other when tightening the loop 55 (see FIG. 2B). Accordingly, the tension limiter 102 can be configured apply a force that is greater than, but corresponds to, the tension in the loop 55 about the target bone. Thus, the maximum force applied by the tension limiter 102 can correspond to the maximum desired tension in the loop 55, it being appreciated that once the teeth 48 and 58 ride over and past each other, the tension in the loop 55 can decrease somewhat as the teeth 48 and 58 interlock. In accordance with one embodiment, the tension limiter 102 can apply a maximum force as desired, for instance up to approximately 430 Newtons or any other force as desired that corresponds to a desired maximum tension in the loop 55 about the target bone 28. As a result, once the desired maximum tension in the loop 55 has been induced about the target bone 28, the force applied by the tension limiter 102 when the trigger 84 is fully actuated is insufficient to cause the teeth 48 and 58 to ride past each other and further tighten the loop 55. Accordingly, once the maximum tension in the loop 55 has been induced about the target bone 28, the force applied by the tension limiter 102 to the traveler will be insufficient to cause the traveler 98 to translate rearward a sufficient distance that further tightens the loop 55 about the target bone 28. Once the tension in the loop 55 has reached the maximum predetermined tension, the trigger 84 can be released, and the actuation pin 64 can return to the mouth of the slot 68 as illustrated in FIG. 5B.

Referring now to FIGS. 7A-7D, and as described above, the fixation instrument 22 includes the cutter assembly 72 that is configured to sever the free end 35 of the strap 32 after the tension in the loop 55 has reached the maximum predetermined tension. For instance, the toggle member 83 can be moved in the rearward direction away from the body 76 to iterate the fixation device 22 from the tensioning mode to the cutting mode. In particular, the fixation device includes a support arm 105 that is attached to the toggle member 83 at a first end, and supports the pivot pin 67 at a second end that is spaced forward from the first end. It should be appreciated that the support arm 105 can be monolithic with the toggle member 83 as desired. The support arm 105 and the toggle member 83 can define an actuator assembly configured to move in the rearward direction from a first position to a second position. The support arm 105 is supported by the housing 88, and is configured to move between a first forward position and a second rearward position. In one example, the support arm 105 is configured to move along the longitudinal direction L. When the toggle member 83 is at a first position, the support arm 105 is at the first position whereby the pivot pin 67 is at the first position in the slot 66 as described above with respect to FIGS. 5A-5C. When the toggle member 83 moves to the second armed position, the support arm 105 moves along with the toggle member 83 to the respective second position whereby the pivot pin 67 is in the second position is at the second position in the slot 66.

In one example, the toggle member 83 is pulled away from the housing 88 in the rearward direction as it moves from the first position to the second position. The fixation instrument 22 can include an actuator spring member 109 coupled between the support arm 105 and the housing 88. For instance, the actuator spring member 109 can be attached at a first end to the support arm 105, and attached at a second end to one of the fixation members 94 that extends between opposed sides of the housing 88. The second end can be spaced from the first end in the forward direction, but it should be appreciated that the actuator spring member 109 can be configured such that the second end is spaced from the first end in the rearward direction. As the support arm 105 travels in the rearward direction from the first position to the second position, the first end of the actuator spring member 109 moves away from the second end of the actuator spring member 109, thereby expanding the actuator spring member. Accordingly, the actuator spring member 109 applies a spring force to the support arm 105 that biases the support arm 105 in the forward direction. Accordingly, movement of the toggle member 83 in the rearward direction is against the spring force of the actuator spring member 109.

Figure 8A:
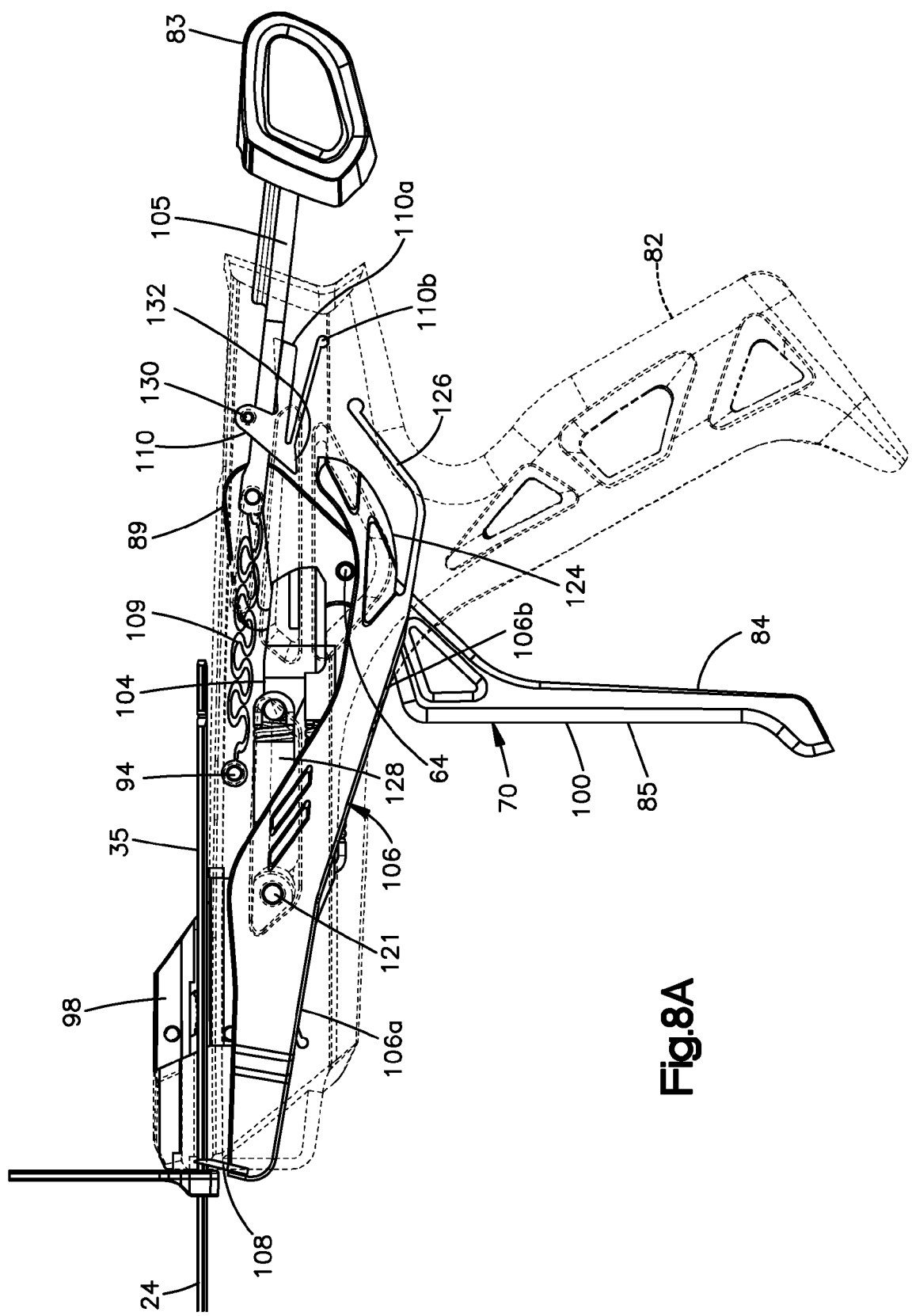
FIG. 8A is a side elevation view of the bone fixation instrument as illustrated in FIG. 7A, but showing the cutting assembly in a cutting configuration.
Figure 8B:
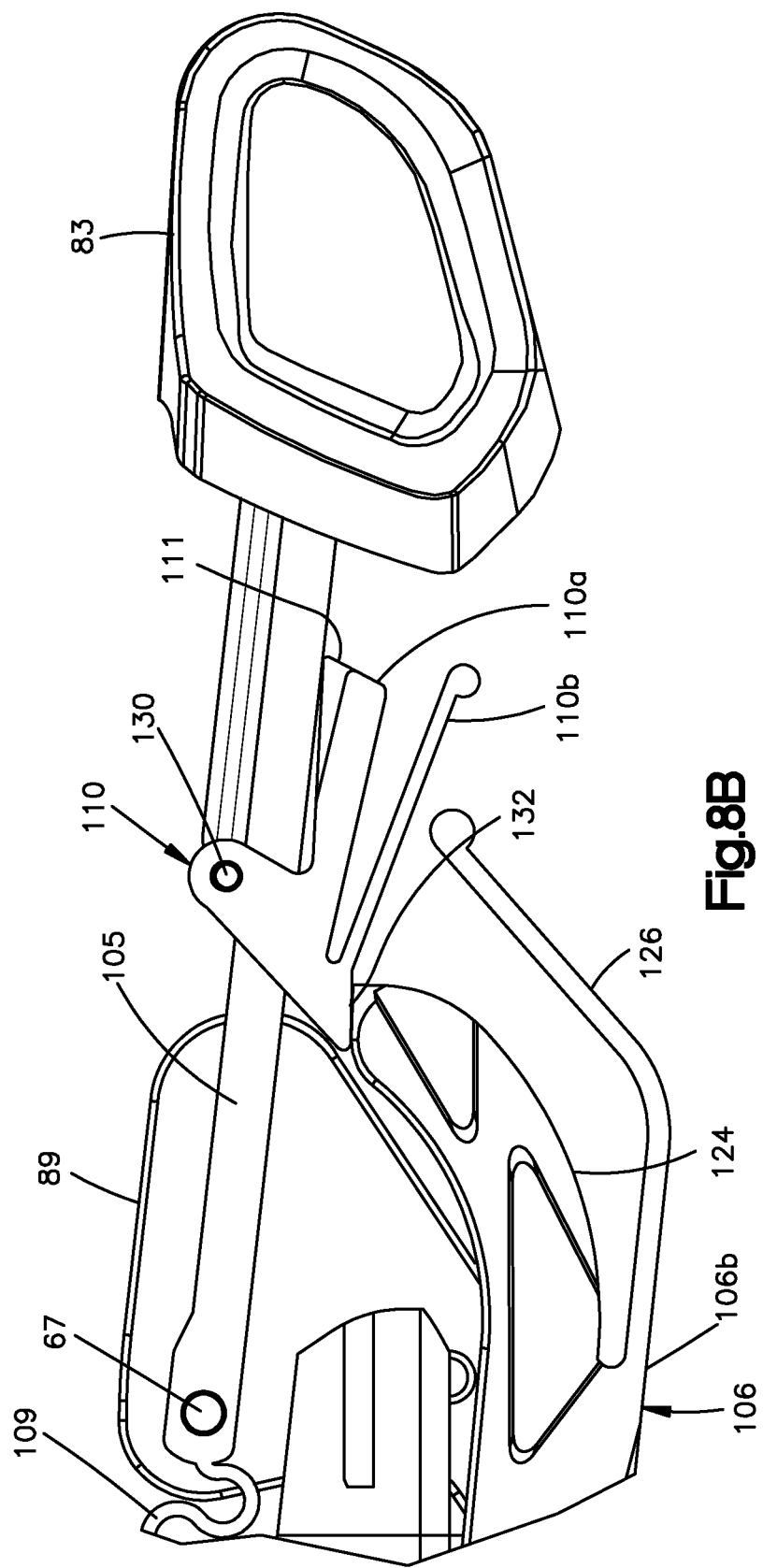
FIG. 8B is an enlarged perspective view of an actuator and a locking member of the cutting assembly, showing the actuator in a first configuration.
Figure 8C:
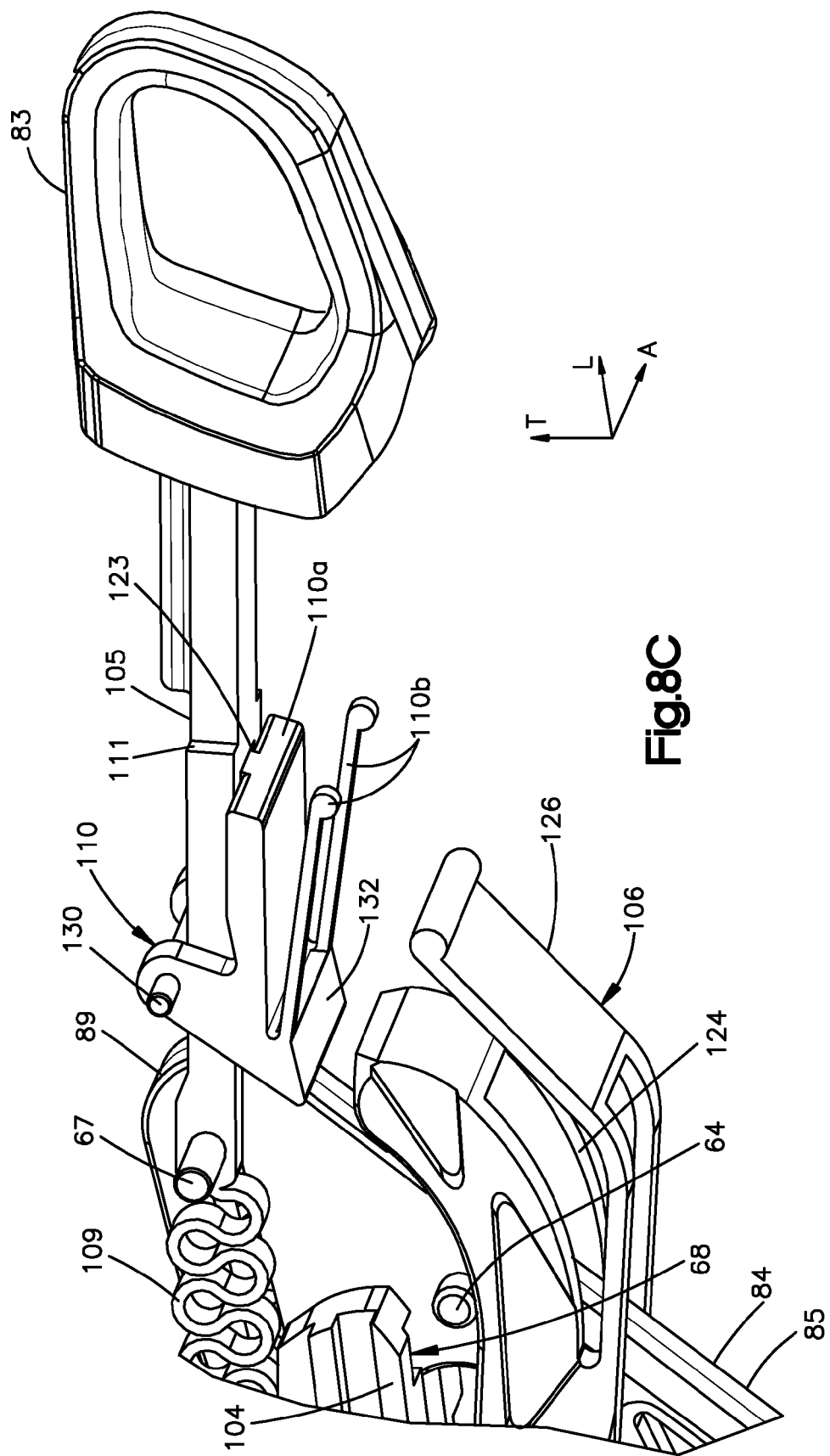
FIG. 8C is an enlarged perspective view similar to FIG. 8B, but showing the actuator in an armed position, and the locking member configured to lock the actuator in the armed position.

Referring also to FIGS. 8B-8C, the fixation instrument 22 includes a locking member 110 that is configured to releasably lock the toggle member 83 in the second position. The locking member 110 can include a locking portion 110*a* and at least one spring portion 110*b* that projects out from the locking portion 110*a* and bears against the housing 88. For instance, the locking member 110 can include a pair of spring portions 110*b* spaced from each other in the lateral direction A. The locking member 110 is pivotally supported by a pivot pin 130 that is supported by the housing 88. The spring portion 110*b* can be compressed so as to bias the locking portion 110*a* against the support arm 105. When the toggle member 83 is moved to the second position, the locking portion 110*a* is configured to engage the support arm 105 so as to prevent the support arm 105 from returning to the first position under the force of the actuator spring member 109. For instance, the locking portion 110*a* can include a projection 111, and the support arm 105 can define an aperture 123 sized to receive the projection. When the support arm 105 and the toggle member 83 are in the first position, the aperture 123 is spaced from the projection 111 in the forward direction, but is aligned with the projection 111 along the longitudinal direction. Accordingly, when the toggle member 83 is moved to the second position, the spring portion 110b causes the locking member 110 to pivot about the pivot pin 130 such that the locking portion 110a is inserted into the aperture 123 under the force of the spring portion 110b. For instance, the projection 111 can be inserted into the aperture 123. As a result, the force of the actuator spring member 109 causes the support arm 105 to bear against the locking portion 110a, thereby preventing the actuator from returning from the second position to the first position.

As illustrated in FIG. 5A, when the trigger 84 is in the first position, the front end 66a of the slot 66 can be disposed above the rear end 66b of the slot 66. Accordingly, referring again to FIGS. 7A-7D, when the pivot pin 67 moves from the first end 66a to the second end 66b in the rearward direction as the actuation arm 105 moves from the first position to the second position, the pivot pin 67 can bias the trigger 84 to pivot about the pivot pin 67 in a second direction opposite the first direction. Accordingly, the actuation pin 64 can move out of the slot 68 such that the actuation pin 64 is disposed adjacent the cutter arm 106. For instance, the actuation pin 64 can move down and out of the slot 68. In one example, the actuation pin 64 can abut the cutter arm 106. Because the actuation pin 64 is disposed out of the slot and out of alignment with the force transfer member 104, movement of the trigger 84 in the first direction from the first position toward the second position does not cause the actuation pin 64 to bear against the force transfer member 104 in the rearward direction. As a result, the trigger 84 is decoupled from the force transfer member 104 when the fixation instrument 22 is in the cutting mode. It should be appreciated that if the bone fixation instrument 22 is devoid of the trigger spring member 146, movement of the pivot pin 67 to the second position can cause the trigger 84 to move about the pivot pin 67 toward the first position whereby the actuation pin 64 moves down out of the slot 68 as described above.

Further, when the pivot pin 67 is disposed at the second position in the slot 66, the pivot pin 67 is offset with respect to the actuation pin 64 in the rearward direction. Thus, the actuator is configured to move about a first pivot axis when the bone fixation instrument is in the tensioning mode, and the actuator moves about a second pivot axis spaced from the first pivot axis in the rearward direction when the bone fixation instrument is in the cutting mode. Accordingly, as illustrated in FIG. 8A, when the trigger 84 is actuated to pivot about the pivot pin 67 in the first direction such that the grip portion 84 moves toward the handle 82, the actuation pin 64 moves down along the transverse direction against the cutter arm 106. The cutter arm 106 includes a front portion 106a and a rear portion 106b spaced from the front portion 106a in the rearward direction. The cutter arm 106 is supported at a cutter pivot pin 121.

The cutter pivot pin 121 is supported by the housing such that the cutter arm 106 is configured to pivot about the cutter pivot pin 121. The front portion 106a extends forward from the cutter pivot pin 121, and the rear portion 106b extends rearward from the cutter pivot pin 121. Thus, the cutter pivot pin 121 is disposed between the front portion 106a and the rear portion 106b. The actuation pin 64 abuts the rear portion 106b of the cutter arm 106. The cutter blade 108a extends from the front portion 106a. For instance, the cutter blade 108a can extend up from the front portion 106a of the cutter arm 106. Accordingly, when the trigger 84 is biased to pivot in the first direction from the first position toward the second position, the actuation pin 64 biases the cutter arm 106 to pivot about the cutter pivot pin 121 in a first cutter direction from a first position to a cut position whereby the cutter blade 108 is brought into contact with the free end 35 of the strap 32, thereby severing the free end 35. For instance, the cutter blade 108 can sever the free end 35 at a location such that the housing 50 is disposed between the loop 55 and the cutting blade 108. In accordance with one embodiment, the cutter blade 108 can be spaced from the nose 86 in the rearward direction. Accordingly, the nose 86 can be disposed between the cutter blade 108 and the housing 50.

Figure 8D:
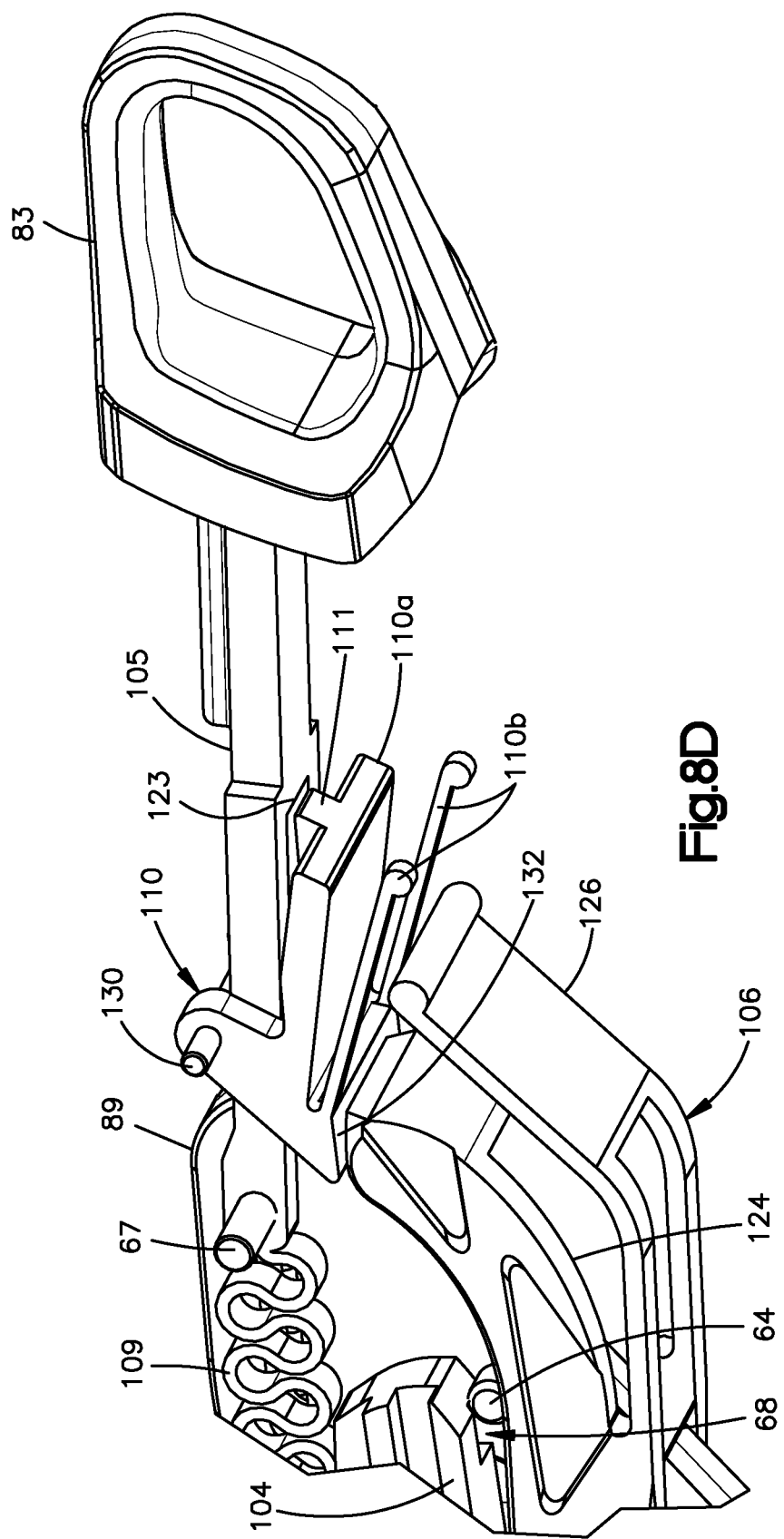
FIG. 8D is an enlarged perspective view similar to FIG. 8C, but showing the actuator and locking member during cutting.
Figure 8E:
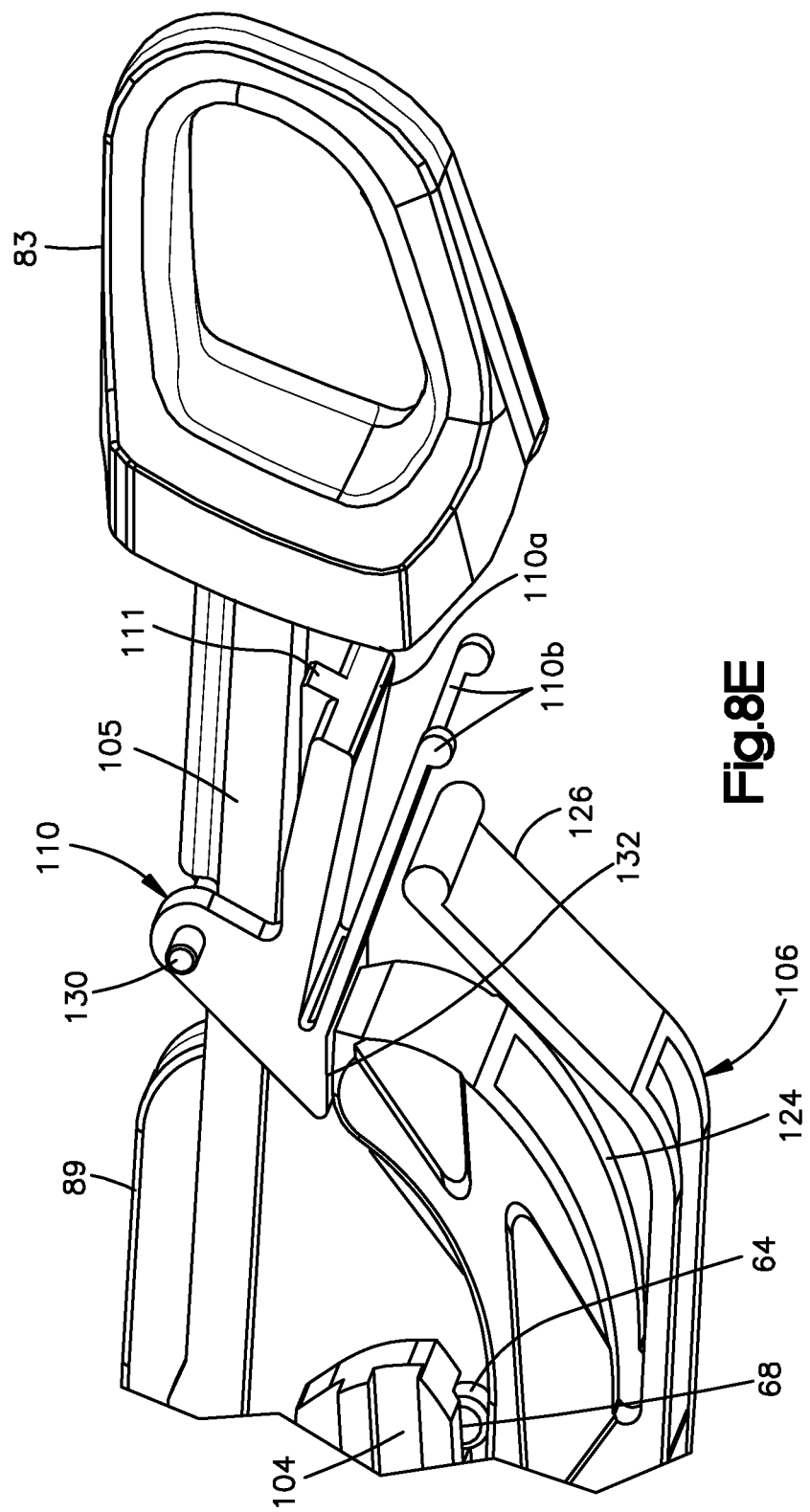
FIG. 8E is an enlarged perspective view similar to FIG. 8D, but showing the actuator returned to a first position upon completion of cutting.

The cutter arm 106 can include a biasing arm 124 and a spring member 126 that each extends out from the rear portion 106b. The spring member 126 can be in the form of a spring arm that bears against the housing 88 so as to bias the cutter arm 106 to pivot in a second cutter direction opposite the first cutter direction about the cutter pivot pin 121. Thus, after the cutter blade 108 has severed the free end 35 and the trigger 84 is released, the spring member 126 biases the cutter pivot pin 121 to pivot in the second cutter direction. Pivoting of the cutter pivot pin 121 in the second cutter direction causes the biasing arm 124 to bear against a bearing surface 132 of the locking member 110. The pivot pin 130 can be disposed rearward of the bearing surface 132, and forward of both the locking portion 110a and the spring portion 110b. As the biasing arm 124 bears against the biasing surface 132, the locking member 110, the locking member is driven to pivot about the pivot pin 130 until the locking portion 110a is removed from the aperture 123. Accordingly, the force of the actuator spring member 109 biases the support arm 105 and the toggle member 83 to move forward as illustrated in FIG. 8D until the pivot pin 67 is disposed in the slot 66 as described above with respect to FIGS. 5A-5C. Thus, the fixation instrument 22 is iterated from the cutting mode to the tensioning mode as described above. It should therefore be appreciated that the fixation instrument 22 does not allow a subsequent actuation of the trigger 84 to move the cutter arm to the cut position without first moving the toggle member 83 to the second position as described above with respect to FIGS. 7A-7D. When the fixation instrument 22 has returned to the tensioning mode, the grip 96 is configured to receive the free end 35 of another strap 32 so as to tension the respective loop 55 and subsequently sever the free end 35 in the manner described above.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone fixation instrument having a front end and a rear end spaced from the front end in a rearward direction, the bone fixation instrument configured to apply tension to a bone fixation member so as to tighten the bone fixation member about a target bone, the bone fixation instrument comprising:
   a grip configured to attach to a free end of the bone fixation member;
   a traveler that supports the grip such that as the traveler moves in the rearward direction, the grip moves along with the traveler in the rearward direction so as to increase tension in the bone fixation member when the grip is attached to the bone fixation member;

a cutter arm that carries a cutter blade and is configured to move the cutter blade to a cutting position whereby the cutter blade severs the free end of the bone fixation member when the grip is attached to the bone fixation member;

an actuator configured to be selectively independently coupled to the traveler and the cutter arm;

a toggle member movable between a first and a second position, wherein 1) when the toggle member is in the first position, the bone fixation instrument is in a tensioning mode whereby movement of the actuator causes the traveler to move in the rearward direction thereby increasing the tension in the bone fixation member when the grip is attached to the bone fixation member, and 2) when the toggle member is in the second position, the bone fixation instrument is in a cutting mode whereby movement of the actuator causes the cutter arm to move the cutter blade to the cutting position; and a force transfer member is coupled to the actuator when the bone fixation member is in the tensioning mode, and decoupled from the actuator when the bone fixation member is in the cutting mode, wherein the actuator defines an actuation pin that is received in a slot of the force transfer member when the bone fixation instrument is in the tensioning mode, and is removed from the slot when the bone fixation instrument is in the cutting mode.

2. The bone fixation instrument as recited in claim 1, wherein when the bone fixation instrument is in the tensioning mode and the grip is attached to the bone fixation member, movement of the actuator causes the traveler to move in the rearward direction until the tension in the bone fixation member reaches a predetermined tension.

3. The bone fixation instrument as recited in claim 2, further comprising a tension limiter coupled between the force transfer member and the traveler.

4. The bone fixation instrument as recited in claim 3, wherein deformation of the tension limiter causes the traveler to move rearward in response to movement of the actuator toward the second position when the tension in the bone fixation member is less than a predetermined tension, and does not cause the traveler to move in the rearward direction in response to movement of the actuator toward the second position when the tension in the bone fixation member reaches the predetermined tension.

5. The bone fixation instrument as recited in claim 3, wherein the tension limiter further causes the traveler to move in a forward direction opposite the rearward direction when the actuator moves from the second position toward the first position while the bone fixation instrument is in the tensioning mode.

6. The bone fixation instrument as recited in claim 5, wherein the grip interlocks with the free end of the bone fixation member while the grip moves in the rearward direction, and the grip rides along the free end of the bone fixation member when the grip moves in the forward direction.

7. The bone fixation instrument as recited in claim 3, wherein the tension limiter comprises a spring member connected between the actuator and the traveler, wherein movement of the actuator causes the spring member to flex and bias the traveler rearward under a biasing force when the bone fixation instrument is in the tensioning mode.

8. The bone fixation instrument as recited in claim 7, wherein the traveler moves rearward when the biasing force is greater than the tension in the bone fixation member.

9. The bone fixation instrument as recited in claim 8, wherein the traveler remains stationary when the biasing force is not greater than the tension in the bone fixation member.

10. The bone fixation instrument as recited in claim 1, wherein the actuator moves about a first axis when the bone fixation instrument is in the tensioning mode, and the actuator moves about a second axis that is spaced from the first axis when the bone fixation instrument is in the cutting mode.

11. The bone fixation instrument as recited in claim 10, wherein the actuator defines a slot that receives a pivot pin, wherein the pivot pin is in a first position when the bone fixation instrument is in the tensioning mode, and the pivot pin is in a second position spaced from the first position in the rearward direction when the bone fixation instrument is in the cutting mode.

12. The bone fixation instrument as recited in claim 1, wherein movement of the toggle member to the second position causes the actuator to abut the cutter arm when the bone fixation instrument is in the cutting mode.

13. The bone fixation instrument as recited in claim 1 wherein the actuation pin abuts the cutting member when the bone fixation instrument is in the cutting mode.

14. The bone fixation instrument as recited in claim 13, wherein movement of the actuator causes the actuation pin to drive the cutting member to move the cutting blade to the cutting position.

15. A bone fixation instrument having a front end and a rear end spaced from the front end in a rearward direction, the bone fixation instrument configured to apply tension to a bone fixation member so as to tighten the bone fixation member about a target bone, the bone fixation instrument comprising:

a grip configured to attach to a free end of the bone fixation member;

a traveler that supports the grip such that as the traveler moves in the rearward direction, the grip moves along with the traveler in the rearward direction so as to increase tension in the bone fixation member when the grip is attached to the bone fixation member;

a cutter arm that carries a cutter blade, the cutter arm configured to move the cutter blade to a cutting position whereby the cutter blade severs the free end of the bone fixation member when the grip is attached to the bone fixation member;

an actuator configured to selectively pivot about a first pivot axis and a second pivot axis that is spaced from the first pivot axis, such that when the actuator pivots about the first pivot axis, the bone fixation instrument is in a tensioning mode whereby the actuator causes a force to be applied to the traveler in the rearward direction, and when the actuator pivots about the second pivot axis, the bone fixation instrument is in a cutting mode whereby the actuator causes a force to be applied to the cutter member, thereby causing the cutter member to move the cutting blade to the cutting position, wherein the actuator defines a slot that receives a pivot pin, wherein the pivot pin is in a first position in the slot so as to define the first pivot axis, and the pivot pin is in a second position in the slot spaced from the first position in the rearward direction so as to define the second pivot axis.

16. The bone fixation instrument as recited in claim 15, wherein the actuator is configured to be selectively independently coupled to the traveler and the cutter arm.

17. The bone fixation instrument as recited in claim 15, wherein the actuator is coupled to the traveler when the actuator pivots about the first pivot axis, and the actuator is coupled to the cutter arm when the actuator pivots about the second pivot axis.

18. The bone fixation instrument as recited in claim 15, wherein the actuator is decoupled from the cutter arm when the actuator pivots about the first pivot axis, and the actuator is decoupled from the traveler when the actuator pivots about the second pivot axis.

19. The bone fixation instrument as recited in claim 15, further comprising a toggle member movable between a first and a second position, wherein 1) when the toggle member is in the first position, the bone fixation instrument is in a tensioning mode whereby movement of the actuator about the first pivot axis causes the traveler to move in the rearward direction until the tension in the bone fixation member reaches a predetermined tension when the grip is attached to the bone fixation member, and 2) when the toggle member is in the second position, the bone fixation instrument is in a cutting mode whereby movement of the actuator about the second pivot axis causes the cutter arm to move the cutter blade to the cutting position.

* * * * *